US008445680B2

(12) United States Patent
Debenham et al.

(10) Patent No.: US 8,445,680 B2
(45) Date of Patent: May 21, 2013

(54) TETRAHYDROTHIENO PYRIDINES

(75) Inventors: John S. Debenham, Scotch Plains, NJ (US); Jeffrey J. Hale, Westfield, NJ (US); Christina B. Madsen-Duggan, Scotch Plains, NJ (US); Thomas F. Walsh, Watchung, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 241 days.

(21) Appl. No.: 12/919,190

(22) PCT Filed: Feb. 11, 2009

(86) PCT No.: PCT/US2009/033718
§ 371 (c)(1),
(2), (4) Date: Aug. 24, 2010

(87) PCT Pub. No.: WO2009/108497
PCT Pub. Date: Sep. 3, 2009

(65) Prior Publication Data
US 2011/0009425 A1 Jan. 13, 2011

Related U.S. Application Data

(60) Provisional application No. 61/066,977, filed on Feb. 25, 2008.

(51) Int. Cl.
C07D 495/04 (2006.01)
A61K 31/4436 (2006.01)
(52) U.S. Cl.
USPC ........................................ 546/114; 514/301
(58) Field of Classification Search
USPC ........................................ 546/114; 514/301
See application file for complete search history.

(56) References Cited

FOREIGN PATENT DOCUMENTS
WO    WO2007/136990 A3    11/2007

OTHER PUBLICATIONS

"Anemia: Prevention, Mayo Clinic" online "http://www.mayoclinic.com/health/anemia/DS00321/DSECTION=prevention Sep. 4, 2012" accessed Sep. 4, 2012.*
West, Anthony R., Solid State Chemistry and its Applications, Wiley, New York, 1988, pp. 358 & 365.*
McDonough et al., Cellular Oxygen Sensing: Crystal structure of hypoxia-inducible factor prolyl hydroxylase (PHD2), PNAS, vol. (103)26, pp. 9814-9819.

* cited by examiner

Primary Examiner — David K O Dell
(74) Attorney, Agent, or Firm — Patricia A. Shatynski; Valerie J. Camara

(57) ABSTRACT

The present invention relates to tetrahydrothienopyridine compounds useful as HIF prolyl hydroxylase inhibitors to treat anemia and like conditions.

14 Claims, No Drawings

TETRAHYDROTHIENO PYRIDINES

CROSS REFERENCE TO RELATED APPLICATIONS

This application is a U.S. National Phase application under 35 U.S.C. §371 of PCT Application No. PCT/US2009/033718, filed Feb. 11, 2009 which claims priority under 35 U.S.C. §119(e) from U.S. Provisional Application Ser. No. 61/066,977, filed Feb. 25, 2008.

BACKGROUND OF THE INVENTION

The insufficient delivery of oxygen to cells and tissues is associated with anemia, which is defined as a deficiency in the blood's oxygen-carrying capacity, and ischemia, in which restrictions in blood supply are caused by a constriction or blockage of blood vessels. Anemia can be caused by the loss of red blood cells (hemorrhage), excessive red blood cell destruction (hemolysis) or deficiencies in erythropoiesis (production of red blood cells from precursors found in the bone marrow). The symptoms of anemia can include weakness, dizziness, fatigue, pallor, impairment of cognitive function and a general reduction in quality of life. Chronic and/or severe anemia can lead to the exacerbation of myocardial, cerebral or peripheral ischemia and to heart failure. Ischemia is defined as an absolute or relative shortage of oxygen to a tissue or organ and can result from disorders such as atherosclerosis, diabetes, thromboembolisms, hypotension, etc. The heart, brain and kidney are especially sensitive to ischemic stress caused by low blood supply.

The primary pharmacological treatment for anemia is administration of some variant of recombinant human erythropoietin (EPO). For anemias associated with kidney disease, chemotherapy-induced anemia, anemia from HIV-therapy or anemia due to blood loss, recombinant EPO is administered to enhance the supply of the hormone, correct the shortage of red blood cells and increase the blood's oxygen-carrying capacity. EPO replacement is not always sufficient to stimulate optimal erythropoiesis (e.g., in patients with iron processing deficiencies) and has associated risks.

Hypoxia-inducible factor (HIF) has been identified as a primary regulator of the cellular response to low oxygen. HIF is a heterodimeric gene transcription factor consisting of a highly regulated α-subunit (HIF-α) and a constitutively expressed β-subunit (HIF-β, also known as ARNT, or aryl hydrocarbon receptor nuclear transporter). HIF target genes are reported to be associated with various aspects of erythropoiesis (e.g., erythropoietin (EPO) and EPO receptor), glycolysis and angiogenesis (e.g., vascular endothelial growth factor (VEGF)). Genes for proteins involved in iron absorption, transport and utilization as well as heme synthesis are also targets of HIF.

Under normal oxygenation, HIF-α is a substrate in a reaction with molecular oxygen, which is catalyzed by a family of iron(II)-, 2-ketoglutarate- and ascorbate-dependent dioxygenase enzymes called PHD-1 (EGLN2, or egg laying abnormal 9 homolog 2, PHD2 (EGLN1), and PHD3 (EGLN3). Proline residues of HIF-α are hydroxylated (e.g., Pro-402 and Pro-564 of HIF-1α) and the resulting product is a target of the tumor suppressor protein von-Hippel Lindau, a component of an E3 ubiquitin ligase multiprotein complex involved in protein ubiquitination. Under low oxygenation, the HIF-α hydroxylation reaction is less efficient and HIF-α is available to dimerize with HIF-β HIF dimers are translocated to the cell nucleus where they bind to a hypoxia-responsive enhancer element of HIF target genes.

Cellular levels of HIF are known to increase under conditions of hypoxia and after exposure to hypoxia mimetic agents. The latter includes, but is not limited to, specific metal ions (e.g., cobalt, nickel, manganese), iron chelators (e.g., desfenioxamine) and analogs of 2-ketoglurate (e.g., N-oxalyl glycine). The compounds of the present invention inhibit the HIF prolyl hydroxylases (PHD-1, PHD-2, PHD-3) and can also serve to modulate HIF levels. These compounds therefore have utility for the treatment and/or prevention of disorders or conditions where HIF modulation is desirable, such as anemia and ischemic. As an alternative to recombinant erythropoietin therapy, the compounds of the present invention provide a simpler and broader method for the management of anemia.

SUMMARY OF THE INVENTION

The present invention concerns compounds of formula I,

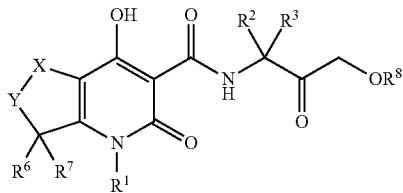

which inhibit HIF prolyl hydroxylase, their use for enhancing endogenous production of erythropoietin, and for treating conditions associated with reduced endogenous production of erythropoietin such as anemia and like conditions, as well as pharmaceutical compositions comprising such a compound and a pharmaceutical carrier.

DETAILED DESCRIPTION OF THE INVENTION

The present invention provides compounds of formula I and pharmaceutically acceptable salts and solvates thereof:

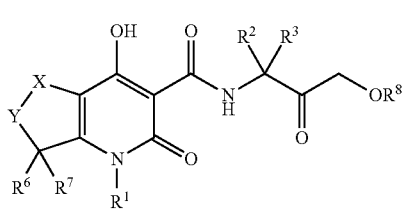

wherein
$R^8$ is selected from hydrogen, $C_{1-6}$ alkyl, optionally substituted with a hydroxy, —SH, —NH$_2$ or —CO$_2$H, and $C_{3-6}$ cycloalkyl optionally substituted with a hydroxy, —SH, —NH$_2$ or —CO$_2$H;
n is 1 or 2;
one of X or Y is —S(O)$_n$, and the other is $CR^4R^5$;
$R^1$ is selected from
  —$C_{1-10}$ alkyl,
  —$C_{2-10}$ alkenyl,
  —$C_{5-10}$ cycloalkenyl,
  —$C_{2-10}$ alkynyl,
  —$C_{0-10}$ alkylaryl,
  —$C_{0-10}$ alkylheterocyclyl;
  —$C_{0-10}$ alkyl-$C_{0-10}$cycloalkyl, and
  perfluoro$C_{1-6}$alkyl;

wherein in $R^1$ said alkyl, alkenyl, alkynyl, cycloalkenyl, aryl, heterocycloalkyl, heterocyclyl, and cycloalkyl are each optionally substituted with one or more $R^9$ substituents;

$R^2$ and $R^3$ are independently selected from hydrogen, phenyl, heterocyclyl, and —$C_{1-10}$ alkyl, wherein $C_{1-10}$ alkyl is unsubstituted or substituted with one or more fluorine atoms, and phenyl is unsubstituted or substituted with or more substituents selected from fluoro, chloro, hydroxyl, $C_{1-10}$ alkyl, and —$OC_{1-10}$ alkyl;

$R^4$, $R^5$, $R^6$, and $R^7$ are independently selected from hydrogen, cyano, oxo, —$C_1$-$C_{10}$ alkyl, —$C_{2-10}$ alkenyl, —$C_{3-10}$ cycloalkyl, —($C_{1-10}$ alkyl)aryl, ($C_{0-10}$ alkyl)heterocyclyl, —$C_{5-10}$ cycloalkenyl, —$C_{2-10}$ alkynyl, —$SO_n(C_{1-10}$ alkyl) and —$SO_n$aryl wherein said alkyl, alkenyl, alkynyl, cycloalkyl, cycloalkenyl, aryl, and heterocyclyl are optionally substituted by one or more substituents $R^9$, and optionally one set of substituents, $R^4$ and $R^5$, or $R^6$ and $R^7$, are linked together to form a ring of 5 to 8 atoms optionally substituted with one or more substituents $R^9$; where said ring is partially or fully unsaturated having 0, 1 or 2 heteroatoms independently selected from —$NR^6$—, —O— and —$S(O)_n$—;

$R^9$ is selected from halogen, hydroxy, oxo, cyano, aryl, heterocyclyl, —$C_{1-6}$ alkyl, —$C_{1-6}$ alkoxy, aryloxy, heterocyclyloxy, —$CO_2R^a$, —$NR^bR^c$, —$CONR^bR^c$, —$OCO_2R^a$, —$OCONR^bR^c$, —$NR^dCO_2R^a$, —$NR^dCONR^bR^c$, —$SC_{0-6}$ alkyl and —$S(O)_nR^d$, wherein said aryl, heterocyclyl, alkoxy, aryloxy, heterocyclyloxy are optionally substituted by one or more substituents $R^{10}$;

$R^{10}$ is selected from hydroxy, aryl, heterocyclyl, halogen, —$C_{1-6}$ alkyl, $C_{1-6}$ alkoxy, halogen, $CO_2H$, cyano, $O(C=O)_{0-1}C_{1-6}$ alkyl, $NO_2$, trifluoromethoxy, trifluoroethoxy, —$O_{0-1})(C_{1-10})$perfluoroalkyl, $C_{0-10}$ alkylaminocarbonylamino, $C_{0-10}$ alkyloxycarbonylamino$C_{0-10}$ alkyl, $C_{0-10}$ alkylcarbonylamino$C_{0-10}$alkyl, $C_{0-10}$ alkylaminosulfonylamino$C_{0-10}$ alkyl, $C_{0-10}$ alkylsulfonylamino$C_{0-10}$ alkyl, $C_{0-10}$ alkylsulfonyl, $C_{0-10}$ alkylaminosulfonyl, $C_{0-10}$ alkylaminocarbonyl, —(C=O)N($C_{0-6}$ alkyl)$_2$, —S($C_{0-6}$ alkyl), and $NH_2$;

$R^a$ is chosen from hydrogen; —$C_{1-10}$ alkyl, —($C_{1-6}$ alkyl)$C_{3-8}$ cycloalkyl; and —($C_{1-6}$ alkyl)phenyl; and $R^b$, $R^c$, and $R^d$ are each independently chosen from hydrogen, —$C_{1-10}$ alkyl, —$C_{3-10}$ cycloalkyl, aryl, and heterocyclyl, wherein said alkyl, cycloalkyl, aryl and heterocyclyl are optionally substituted by one or more substituents $R^{10}$.

Illustrative but nonlimiting examples of compounds of the invention are the following:

N-({1-[(6-chloropyridin-3-yl)methyl]-4-hydroxy-2-oxo-1,2,5,7-tetrahydrothieno[3,4-b]pyridin-3-yl}carbonyl)glycine;

N-{[1-(4-bromobenzyl)-4-hydroxy-2-oxo-1,2,5,7-tetrahydrothieno[3,4-b]pyridin-3-yl]carbonyl}glycine;

N-{([1-(4-cyanobenzyl)-4-hydroxy-2-oxo-1,2,5,7-tetrahydrothieno[3,4-b]pyridin-3-yl]carbonyl}glycine;

N-({4-hydroxy-2-oxo-1-[4-(trifluoromethyl)benzyl]-1,2,5,7-tetrahydrothieno[3,4-b]pyridin-3-yl}carbonyl)glycine;

N-[(4-hydroxy-2-oxo-1-{[6-(trifluoromethyl)pyridin-3-yl]methyl}-1,2,5,7-tetrahydrothieno[3,4-b]pyridin-3-yl)carbonyl]glycine;

N-({4-hydroxy-1-[4-(methylsulfonyl)benzyl]-2-oxo-1,2,5,7-tetrahydrothieno[3,4-b]pyridin-3-yl}carbonyl)glycine;

N-({4-hydroxy-2-oxo-1-[(4-phenyl-1,3-thiazol-2-yl)methyl]-1,2,5,7-tetrahydrothieno[3,4-b]pyridin-3-yl}carbonyl)glycine N-{[4-hydroxy-1-(4-isopropylbenzyl)-2-oxo-1,2,5,7-tetrahydrothieno[3,4-b]pyridin-3-yl]carbonyl}glycine;

N-{[1-(4-tert-butylbenzyl)-4-hydroxy-2-oxo-1,2,5,7-tetrahydrothieno[3,4-b]pyridin-3-yl]carbonyl}glycine;

N-({4-hydroxy-2-oxo-1-[(5-phenyl-1,2,4-oxadiazol-3-yl)methyl]-1,2,5,7-tetrahydrothieno[3,4-b]pyridin-3-yl}carbonyl)glycine;

N-{[1-(1,3-benzothiazol-2-ylmethyl)-4-hydroxy-2-oxo-1,2,5,7-tetrahydrothieno[3,4-b]pyridin-3-yl]carbonyl}glycine;

N-{[1-(4-bromophenyl)-4-hydroxy-2-oxo-1,2,5,7-tetrahydrothieno[3,4-b]pyridin-3-yl]carbonyl}glycine;

N-({1-[3-fluoro-5-(trifluoromethyl)benzyl]-4-hydroxy-2-oxo-1,2,5,7-tetrahydrothieno[3,4-b]pyridin-3-yl}carbonyl)glycine;

N-{[1-(3-chlorobenzyl)-4-hydroxy-2-oxo-1,2,5,7-tetrahydrothieno[3,4-b]pyridin-3-yl]carbonyl}glycine;

N-{[1-(4-chloro-2-methylbenzyl)-4-hydroxy-2-oxo-1,2,5,7-tetrahydrothieno[3,4-b]pyridin-3-yl]carbonyl}glycine;

N-{([1-(4-chlorobenzyl)-4-hydroxy-2-oxo-1,2,5,7-tetrahydrothieno[3,4-b])]pyridin-3-yl]carbonyl}glycine;

N-{[1-(4-ethylbenzyl)-4-hydroxy-2-oxo-1,2,5,7-tetrahydrothieno[3,4-b]pyridin-3-yl]carbonyl}glycine;

N-({1-[4-chloro-3-(trifluoromethyl)benzyl]-4-hydroxy-2-oxo-1,2,5,7-tetrahydrothieno[3,4-b]pyridin-3-yl}carbonyl)glycine;

N-{[1-(3,4-dichlorobenzyl)-4-hydroxy-2-oxo-1,2,5,7-tetrahydrothieno[3,4-b]pyridin-3-yl]carbonyl}glycine;

N-({4-hydroxy-2-oxo-1-[4-(trifluoromethoxy)benzyl]-1,2,5,7-tetrahydrothieno[3,4-b]pyridin-3-yl}carbonyl)glycine;

N-({4-hydroxy-2-oxo-1-[(2-phenyl-1,3-oxazol-4-yl)methyl]-1,2,5,7-tetrahydrothieno[3,4-b]pyridin-3-yl}carbonyl)glycine;

N-{[1-(1-benzothien-2-ylmethyl)-4-hydroxy-2-oxo-1,2,5,7-tetrahydrothieno[3,4-b]pyridin-3-yl]carbonyl}glycine;

N-({4-hydroxy-2-oxo-1-[4-(1H-pyrazol-1-yl)benzyl]-1,2,5,7-tetrahydrothieno[3,4-b]pyridin-3-yl}carbonyl)glycine;

N-({4-hydroxy-2-oxo-1-[(1-phenyl-1H-pyrazol-4-yl)methyl]-1,2,5,7-tetrahydrothieno[3,4-b]pyridin-3-yl}carbonyl)glycine;

N-({4-hydroxy-1-[(4'-methylbiphenyl-4-yl)methyl]-2-oxo-1,2,5,7-tetrahydrothieno[3,4-b]pyridin-3-yl}carbonyl)glycine;

N-[(1-{[5-(2-fluorophenyl)pyrazin-2-yl]methyl}-4-hydroxy-2-oxo-1,2,5,7-tetrahydrothieno[3,4-b]pyridin-3-yl)carbonyl]glycine;

N-({4-hydroxy-2-oxo-1-[4-(1H-pyrazol-5-yl)benzyl]-1,2,5,7-tetrahydrothieno[3,4-b]pyridin-3-yl}carbonyl)glycine;

N-({1-[(4'-acetylbiphenyl-4-yl)methyl]-4-hydroxy-2-oxo-1,2,5,7-tetrahydrothieno[3,4-b]pyridin-3-yl}carbonyl)glycine;

N-{[1-(biphenyl-4-ylmethyl)-4-hydroxy-2-oxo-1,2,5,7-tetrahydrothieno[3,4-b]pyridin-3-yl]carbonyl}glycine;

N-({1-[(4'-chlorobiphenyl-4-yl)methyl]-4-hydroxy-2-oxo-1,2,5,7-tetrahydrothieno[3,4-b]pyridin-3-yl}carbonyl)glycine;

N-({1-[4-(3,5-dimethyl-1H-pyrazol-4-yl)benzyl]-4-hydroxy-2-oxo-1,2,5,7-tetrahydrothieno[3,4-b]pyridin-3-yl}carbonyl)glycine;

N-({1-[4-(4-fluorophenoxy)benzyl]-4-hydroxy-2-oxo-1,2,5,7-tetrahydrothieno[3,4-b]pyridin-3-yl}carbonyl)glycine;

N-({1-[4-(4-chlorophenoxy)benzyl]-4-hydroxy-2-oxo-1,2,5,7-tetrahydrothieno[3,4-b]pyridin-3-yl}carbonyl)glycine;

N-({1-[(4'-ethoxybiphenyl-4-yl)methyl]-4-hydroxy-2-oxo-1,2,5,7-tetrahydrothieno[3,4-b]pyridin-3-yl}carbonyl)glycine;

N-({4-hydroxy-2-oxo-1-[4-(2-thienyl)benzyl]-1,2,5,7-tetrahydrothieno[3,4-b]pyridin-3-yl}carbonyl)glycine;

N-[(4-hydroxy-2-oxo-1-{[4'-(trifluoromethoxy)biphenyl-4-yl]methyl}-1,2,5,7-tetrahydrothieno[3,4-b]pyridin-3-yl)carbonyl]glycine;

N-{[1-({2'-[(diethylamino)carbonyl]biphenyl-4-yl}methyl)-4-hydroxy-2-oxo-1,2,5,7-tetrahydrothieno[3,4-b]pyridin-3-yl]carbonyl}glycine;

N-({4-hydroxy-2-oxo-1-[4'-(trifluoromethoxy)biphenyl-4-yl]-1,2,5,7-tetrahydrothieno[3,4-b]pyridin-3-yl}carbonyl)glycine;

N-{(1-{[6-(3-chlorophenyl)pyridinium-3-yl]methyl}-4-hydroxy-2-oxo-1,2,5,7-tetrahydrothieno[3,4-b]pyridin-3-yl)carbonyl]glycine trifluoroacetate;

N-[(1-{[6-(4-fluorophenyl)pyridinium-3-yl]methyl}-4-hydroxy-2-oxo-1,2,5,7-tetrahydrothieno[3,4-b]pyridin-3-yl)carbonyl]glycine trifluoroacetate;

N-[(1-{[6-(2-chlorophenyl)pyridinium-3-yl]methyl}-4-hydroxy-2-oxo-1,2,5,7-tetrahydrothieno[3,4-b]pyridin-3-yl)carbonyl]glycine trifluoroacetate;

N-({4-hydroxy-2-oxo-1-[3'-(trifluoromethoxy)biphenyl-4-yl]-1,2,5,7-tetrahydrothieno[3,4-b]pyridin-3-yl}carbonyl)glycine;

N-[(1-{[6-(2-fluorophenyl)pyridin-3-yl]methyl}-4-hydroxy-2-oxo-1,2,5,7-tetrahydrothieno[3,4-b]pyridin-3-yl)carbonyl]glycine;

N-{[4-hydroxy-2-oxo-1-({6-[4-(trifluoromethyl)phenyl]pyridinium-3-yl}methyl)-1,2,5,7-tetrahydrothieno[3,4-b]pyridin-3-yl]carbonyl}glycine trifluoroacetate;

N-{[4-hydroxy-2-oxo-1-({6-[2-(trifluoromethyl)phenyl]pyridinium-3-yl}methyl)-1,2,5,7-tetrahydrothieno[3,4-b]pyridin-3-yl]carbonyl}glycine trifluoroacetate;

N-({1-[3'-cyanobiphenyl-4-yl)methyl]-4-hydroxy-2-oxo-1,2,5,7-tetrahydrothieno[3,4-b]pyridin-3-yl}carbonyl)glycine;

N-{[4-hydroxy-1-({6-[2-(methylthio)phenyl]pyridinium-3-yl}methyl)-2-oxo-1,2,5,7-tetrahydrothieno[3,4-b]pyridin-3-yl]carbonyl}glycine trifluoroacetate;

N-[(4-hydroxy-1-{[6-(2-methylphenyl)pyridinium-3-yl]methyl}-2-oxo-1,7-tetrahydrothieno[3,4-b]pyridin-3-yl)carbonyl]glycine trifluoroacetate;

N-{[4-hydroxy-2-oxo-1-({6-[3-(trifluoromethoxy)phenyl]pyridinium-3-yl}methyl)-1,2,5,7-tetrahydrothieno[3,4-b]pyridin-3-yl]carbonyl}glycine trifluoroacetate;

N-[(1-{[6-(2-ethylphenyl)pyridinium-3-yl]methyl}-4-hydroxy-2-oxo-1,2,5,7-tetrahydrothieno[3,4-b]pyridin-3-yl)carbonyl]glycine trifluoroacetate;

N-[(1-{[6-(2,5-difluorophenyl)pyridinium-3-yl]methyl}-4-hydroxy-2-oxo-1,2,5,7-tetrahydrothieno[3,4-b]pyridin-3-yl)carbonyl]glycine trifluoroacetate;

N-{[4-hydroxy-2-oxo-1-(4-quinolinium-5-ylbenzyl)-1,2,5,7-tetrahydrothieno[3,4-b]pyridin-3-yl]carbonyl}glycine chloride;

N-[(1-{[5-(2-chlorophenyl)pyrazin-2-yl]methyl}-4-hydroxy-2-oxo-1,2,5,7-tetrahydrothieno[3,4-b]pyridin-3-yl)carbonyl]glycine;

N-[(4-hydroxy-1-{[5-(2-methylphenyl)pyrazin-2-yl]methyl}-2-oxo-1,2,5,7-tetrahydrothieno[3,4-b]pyridin-3-yl)carbonyl]glycine;

N-{[4-hydroxy-1-({5-[2-(methylthio)phenyl]pyrazin-2-yl}methyl)-2-oxo-1,2,5,7-tetrahydrothieno[3,4-b]pyridin-3-yl]carbonyl}glycine;

N-[(1-{[5-(2,5-difluorophenyl)pyrazin-2-yl]methyl}-4-hydroxy-2-oxo-1,2,5,7-tetrahydrothieno[3,4-b]pyridin-3-yl)carbonyl]glycine;

N-{[4-hydroxy-2-oxo-1-({5-[2-(trifluoromethyl)phenyl]pyrazin-2-yl}methyl)-1,2,5,7-tetrahydrothieno[3,4-b]pyridin-3-yl]carbonyl}glycine;

N-({4-hydroxy-1-[(4'-methylbiphenyl-4-yl)methyl]-6,6-dioxido-2-oxo-1,2,5,7-tetrahydrothieno[3,4-b]pyridin-3-yl}carbonyl)glycine;

N-({4-hydroxy-1-[(4'-methylbiphenyl-4-yl)methyl]-6-oxido-2-oxo-1,2,5,7-tetrahydrothieno[3,4-b]pyridin-3-yl}carbonyl)glycine;

N-{[1-(4-chlorobenzyl)-4-hydroxy-6,6-dioxido-2-oxo-1,2,5,7-tetrahydrothieno[3,4-b]pyridin-3-yl]carbonyl}glycine;

N-{[4-hydroxy-1-(4-isopropylbenzyl)-6,6-dioxido-2-oxo-1,2,5,7-tetrahydrothieno[3,4-b]pyridin-3-yl]carbonyl}glycine;

N-({4-hydroxy-6,6-dioxido-2-oxo-1-[(4-phenyl-1,3-thiazol-2-yl)methyl]-1,2,5,7-tetrahydrothieno[3,4-b]pyridin-3-yl}carbonyl)glycine, N-({4-hydroxy-6,6-dioxido-2-oxo-1-[4-(trifluoromethyl)benzyl]-1,2,5,7-tetrahydrothieno[3,4-b]pyridin-3-yl}carbonyl)glycine;

N-{[1-(biphenyl-4-ylmethyl)-4-hydroxy-6,6-dioxido-2-oxo-1,2,5,7-tetrahydrothieno[3,4-b]pyridin-3-yl]carbonyl}glycine;

N-({4-hydroxy-6,6-dioxido-2-oxo-1-[4-(trifluoromethoxy)benzyl]-1,2,5,7-tetrahydrothieno[3,4-b]pyridin-3-yl}carbonyl)glycine;

N-{[1-(4-ethylbenzyl)-4-hydroxy-6,6-dioxido-2-oxo-1,2,5,7-tetrahydrothieno[3,4-b]pyridin-3-yl]carbonyl}glycine; and pharmaceutically acceptable salts and solvates thereof:

As used herein except where noted, "alkyl" is intended to include both branched- and straight-chain saturated aliphatic hydrocarbon groups, including all isomers, having the specified number of carbon atoms. Commonly used abbreviations for alkyl groups are used throughout the specification, e.g. methyl may be represented by "Me" or $CH_3$, ethyl may be represented by "Et" or $CH_2CH_3$, propyl may be represented by "Pr" or $CH_2CH_2CH_3$, butyl may be represented by "Bu" or $CH_2CH_2CH_2CH_3$, etc. "$C_{1-6}$ alkyl" (or "$C_1$-$C_6$ alkyl") for example, means linear or branched chain alkyl groups, including all isomers, having the specified number of carbon atoms. $C_{1-6}$ alkyl includes all of the hexyl alkyl and pentyl alkyl isomers as well as n-, iso-, sec- and t-butyl, n- and isopropyl, ethyl and methyl. "$C_{1-4}$ alkyl" means n-, iso-, sec- and t-butyl, n- and isopropyl, ethyl and methyl. The term "alkylene" refers to both branched- and straight-chain saturated aliphatic hydrocarbon groups, including all isomers, having the specified number of carbons, and having two terminal end chain attachments. For illustration, the term "unsubstituted A-$C_4$alkylene-B" represents A-$CH_2$—$CH_2$—$CH_2$—$CH_2$—B. The term "alkoxy" represents a linear or branched alkyl group of indicated number of carbon atoms attached through an oxygen bridge.

Unless otherwise specifically noted as only "unsubstituted" or only "substituted", or when substituents are enumerated, alkyl (either as a stand alone radical or as part of a radical such as alkoxy, alkylthio and aralkyl) groups are unsubstituted or substituted with 1 to 3 substituents on each carbon atom, with halo, $C_1$-$C_{20}$ alkyl, $CF_3$, $NH_2$, $N(C_1$-$C_6$ alkyl$)_2$, $NO_2$, oxo, CN, $N_3$, —OH, —O($C_1$-$C_6$ alkyl), $C_3$-$C_{10}$ cycloalkyl, $C_2$-$C_6$ alkenyl, $C_2$-$C_6$ alkynyl, ($C_0$-$C_6$ alkyl) S(O)$_{0-2}$—, ($C_0$-$C_6$ alkyl)S(O)$_{0-2}$($C_0$-$C_6$ alkyl)-, ($C_0$-$C_6$ alkyl)C(O)NH—, $H_2$N—C(NH)—, —O($C_1$-$C_6$ alkyl)$CF_3$, ($C_0$-$C_6$ alkyl)C(O)—, ($C_0$-$C_6$ alkyl)OC(O)—, ($C_0$-$C_6$ alkyl)O($C_1$-$C_6$ alkyl)-, ($C_0$-$C_6$ alkyl)C(O)$_{1-2}$($C_0$-$C_6$ alkyl)-, ($C_0$-$C_6$ alkyl)OC(O)NH—, —NH($C_1$-$C_6$ alkyl)NHC(O)—NH($C_1$-$C_6$ alkyl), NHC(O)OC$_1$-C$_6$ alkyl, —NH(C$_1$-C$_6$ alkyl)NHSO$_2$(C$_1$-C$_6$ alkyl), —(C$_0$-C$_6$ alkyl)NHSO$_2$(C$_1$-C$_6$ alkyl), aryl, aralkyl, heterocycle, heterocyclylalkyl, halo-aryl, halo-aralkyl, halo-heterocycle, halo-heterocyclylalkyl, cyano-aryl, cyano-aralkyl, cyano-heterocycle and cyano-heterocyclylalkyl.

The term "C$_0$" as employed in expressions such as "C$_{0-6}$ alkyl" means a direct covalent bond; or when the term appears at the terminus of a substituent, C$_{0-6}$ alkyl means hydrogen or C1-6alkyl. Similarly, when an integer defining the presence of a certain number of atoms in a group is equal to zero, it means that the atoms adjacent thereto are connected directly by a bond. For example, in the structure

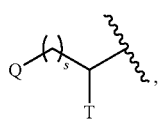

wherein s is an integer equal to zero, 1 or 2, the structure is

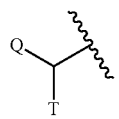

when s is zero.

The term "C$_{3-8}$ cycloalkyl" (or "C$_3$-C$_8$ cycloalkyl") means a cyclic ring of an alkane having three to eight total carbon atoms (i.e., cyclopropyl, cyclobutyl, cyclopentyl, cyclohexyl, cycloheptyl, or cyclooctyl). The terms "C$_{3-7}$ cycloalkyl", "C$_{3-6}$ cycloalkyl", "C$_{5-7}$ cycloalkyl" and the like have analogous meanings.

The term "halogen" (or "halo") refers to fluorine, chlorine, bromine and iodine (alternatively referred to as fluoro (F), chloro (Cl), bromo (Br), and iodo (I)).

The term "aryl" refers to aromatic mono- and poly-carbocyclic ring systems, wherein the individual carbocyclic rings in the polyring systems are fused or attached to each other via a single bond. Suitable aryl groups include phenyl, naphthyl, and biphenylenyl.

The term "carbocycle" (and variations thereof such as "carbocyclic" or "carbocyclyl") as used herein, unless otherwise indicated, refers to (i) a C$_3$ to C$_8$ monocyclic, saturated or unsaturated ring or (ii) a C$_7$ to C$_{12}$ bicyclic saturated or unsaturated ring system. Each ring in (ii) is either independent of, or fused to, the other ring, and each ring is saturated or unsaturated. The carbocycle may be attached to the rest of the molecule at any carbon atom which results in a stable compound. The fused bicyclic carbocycles are a subset of the carbocycles; i.e., the term "fused bicyclic carbocycle" generally refers to a C$_7$ to C$_{10}$ bicyclic ring system in which each ring is saturated or unsaturated and two adjacent carbon atoms are shared by each of the rings in the ring system. A fused bicyclic carbocycle in which one ring is saturated and the other is saturated is a saturated bicyclic ring system. A fused bicyclic carbocycle in which one ring is benzene and the other is saturated is an unsaturated bicyclic ring system. A fused bicyclic carbocycle in which one ring is benzene and the other is unsaturated is an unsaturated ring system. Saturated carbocyclic rings are also referred to as cycloalkyl rings, e.g., cyclopropyl, cyclobutyl, etc. Unless otherwise noted, carbocycle is unsubstituted or substituted with C$_{1-6}$ alkyl, C$_{1-6}$ alkenyl, C$_{1-6}$ alkynyl, aryl, halogen, NH$_2$ or OH. A subset of the fused bicyclic unsaturated carbocycles are those bicyclic carbocycles in which one ring is a benzene ring and the other ring is saturated or unsaturated, with attachment via any carbon atom that results in a stable compound. Representative examples of this subset include the following:

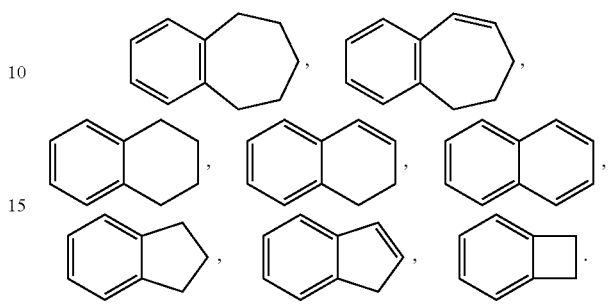

The term "heterocycle" (and variations thereof such as "heterocyclic" or "heterocyclyl") broadly refers to (i) a stable 4- to 8-membered, saturated or unsaturated monocyclic ring, or (ii) a stable 7- to 12-membered bicyclic ring system, wherein each ring in (ii) is independent of, or fused to, the other ring or rings and each ring is saturated or unsaturated, and the monocyclic ring or bicyclic ring system contains one or more heteroatoms (e.g., from 1 to 6 heteroatoms, or from 1 to 4 heteroatoms) selected from N, O and S and a balance of carbon atoms (the monocyclic ring typically contains at least one carbon atom and the ring systems typically contain at least two carbon atoms); and wherein any one or more of the nitrogen and sulfur heteroatoms is optionally oxidized, and any one or more of the nitrogen heteroatoms is optionally quaternized. Unless otherwise specified, the heterocyclic ring may be attached at any heteroatom or carbon atom, provided that attachment results in the creation of a stable structure. Unless otherwise specified, when the heterocyclic ring has substituents, it is understood that the substituents may be attached to any atom in the ring, whether a heteroatom or a carbon atom, provided that a stable chemical structure results.

Non limiting examples of heterocyclylic moieties include, but are not limited to, the following: azabenzimidazole, benzoimidazolyl, benzofuranyl, benzofurazanyl, benzopyrazolyl, benzothiazolyl, benzothienyl, benzotriazolyl, benzothiophenyl, benzoxazolyl, carbazolyl, carbolinyl, chromanyl, cinnolinyl, furanyl, imidazolyl, indolinyl, indolyl, indolazinyl, indazolyl, isobenzofuranyl, isochromanyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridinyl, pyrimidyl, pyrrolyl, quinazolinyl, quinolyl, quinoxalinyl, quinoxalinyl, tetrahydropyranyl, tetrazolyl, tetrazolopyridyl, thiadiazolyl, thiazolyl, thienyl, triazolyl, azetidinyl, aziridinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, tetrahydroquinolinyl, tetrahydroisoquinolinyl, dihydropyrimidinyl, dihydropyrrolyl, dihydroquinolinyl, dihydrotetrazolyl, dihydrothiadiazolyl, dihydrothiazolyl, dihydrothienyl, dihydrothiazolyl, dihydroazetidinyl, methylenedioxybenzoyl, tetrahydrofuranyl, tetrahydrothienyl, tetrahidroquinolinyl, 2,3-dihydrobenzofuranyl, 2,3-dihydrobenzo-1,4-dioxinyl, imidazo(2,1-b)(1,3)thiazole, and benzo-1,3-dioxolyl.

Saturated heterocyclics form a subset of the heterocycles; i.e., the term "saturated heterocyclic" generally refers to a heterocycle as defined above in which the entire ring system (whether mono- or poly-cyclic) is saturated. The term "saturated heterocyclic ring" refers to a 4- to 8-membered saturated monocyclic ring or a stable 7- to 12-membered bicyclic ring system which consists of carbon atoms and one or more heteroatoms selected from N, O and S. Representative examples include piperidinyl, piperazinyl, azepanyl, pyrrolidinyl, pyrazolidinyl, imidazolidinyl, oxazolidinyl, isoxazolidinyl, morpholinyl, thiomorpholinyl, thiazolidinyl, isothiazolidinyl, and tetrahydrofuryl (or tetrahydrofuranyl).

Heteroaromatics form another subset of the heterocycles; i.e., the term "heteroaromatic" (alternatively "heteroaryl") generally refers to a heterocycle as defined above in which the entire ring system (whether mono- or poly-cyclic) is an aromatic ring system. The term "heteroaromatic ring" refers a 5- or 6-membered monocyclic aromatic ring or a 7- to 12-membered bicyclic which consists of carbon atoms and one or more heteroatoms selected from N, O and S. In the case of substituted heteroaryl rings containing at least one nitrogen atom (e.g., pyridine), such substitutions can be those resulting in N-oxide formation. Representative examples of heteroaromatic rings include pyridyl, pyrrolyl, pyrazinyl, pyrimidinyl, pyridazinyl, thienyl (or thiophenyl), thiazolyl, furanyl, imidazolyl, pyrazolyl, triazolyl, tetrazolyl, oxazolyl, isooxazolyl, oxadiazolyl, thiazolyl, isothiazolyl, and thiadiazolyl.

Representative examples of bicyclic heterocycles include benzotriazolyl, indolyl, isoindolyl, indazolyl, indolinyl, isoindolinyl, quinoxalinyl, quinazolinyl, cinnolinyl, chromanyl, isochromanyl, tetrahydroquinolinyl, quinolinyl, tetrahydroisoquinolinyl, isoquinolinyl, 2,3-dihydrobenzofuranyl, 2,3-dihydrobenzo-1,4-dioxinyl (i.e.,

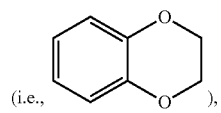

(i.e., ), imidazo(2,1-b)(1,3)thiazole, (i.e.,

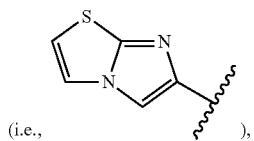 [SMILES: *c1cn2ccsc2n1]

(i.e., ), and benzo-1,3-dioxolyl (i.e.,

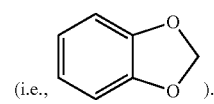

(i.e., ).

In certain contexts herein,

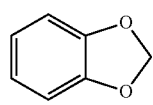

is alternatively referred to as phenyl having as a substituent methylenedioxy attached to two adjacent carbon atoms.

The terms "arylalkyl" and "alkylaryl" include an alkyl portion where alkyl is as defined above and include an aryl portion where aryl is as defined above. Examples of arylalkyl include, but are not limited to, benzyl, phenylethyl, phenylpropyl, naphthylmethyl, and naphthylethyl. Examples of alkylaryl include, but are not limited to, toluene, ethylbenzene, propylbenzene, methylpyridine, ethylpyridine, propylpyridine and butylpyridine.

Unless otherwise specifically noted as only "unsubstituted" or only "substituted", or when substituents are specifically enumerated, cycloalkyl, aryl (including phenyl) and heterocycle (including heteroaryl) groups are unsubstituted or substituted. As used herein, the terms "substituted $C_3$-$C_{10}$ cycloalkyl", "substituted aryl (including phenyl)" and "substituted heterocycle" are intended to include the cyclic group containing from 1 to 3 substituents in addition to the point of attachment to the rest of the compound. Preferably, the substituents are selected from the group which includes, but are not limited to, halo, $C_1$-$C_{20}$ alkyl, $CF_3$, $NH_2$, $N(C_1$-$C_6$ alkyl)$_2$, $NO_2$, oxo, CN, $N_3$, —OH, —O($C_1$-$C_6$ alkyl), $C_3$-$C_{10}$ cycloalkyl, $C_2$-$C_6$ alkenyl, $C_2$-$C_6$ alkynyl, ($C_0$-$C_6$ alkyl) S(O)$_{0-2}$—, aryl-S(O)$_{0-2}$—, ($C_0$-$C_6$ alkyl)S(O)$_{0-2}$($C_0$-$C_6$ alkyl)-, ($C_0$-$C_6$ alkyl)C(O)NH—, $H_2N$—C(NH)—, —O($C_1$-$C_6$ alkyl)CF$_3$, ($C_0$-$C_6$ alkyl)C(O)—, ($C_0$-$C_6$ alkyl)OC(O)—, ($C_0$-$C_6$ alkyl)$_2$NC(O)—($C_0$-$C_6$alkyl)O($C_1$-$C_6$ alkyl)-, ($C_0$-$C_6$ alkyl)C(O)$_{1-2}$($C_0$-$C_6$ alkyl)-, ($C_0$-$C_6$ alkyl)OC(O)NH—, aryl, aralkyl, heteroaryl, heterocyclylalkyl, halo-aryl, halo-aralkyl, halo-heterocycle, halo-heterocyclylalkyl, cyano-aryl, cyano-aralkyl, cyano-heterocycle and cyano-heterocyclylalkyl.

Unless expressly stated to the contrary, an "unsaturated" ring is a partially or fully unsaturated ring. For example, an "unsaturated monocyclic $C_6$ carbocycle" refers to cyclohexene, cyclohexadiene, and benzene.

Unless expressly stated to the contrary, all ranges cited herein are inclusive. For example, a heterocycle described as containing from "1 to 4 heteroatoms" means the heterocycle can contain 1, 2, 3 or 4 heteroatoms.

When any variable occurs more than one time in any constituent or in any formula depicting and describing compounds of the invention, its definition on each occurrence is independent of its definition at every other occurrence. Also, combinations of substituents and/or variables are permissible only if such combinations result in stable compounds.

The term "substituted" (e.g., as in "aryl which is optionally substituted with one or more substituents . . . ") includes mono- and poly-substitution by a named substituent to the extent such single and multiple substitution (including multiple substitution at the same site) is chemically allowed.

The term "oxy" means an oxygen (O) atom. The term "thio" means a sulfur (S) atom. The term "oxo" means "=O". The term "carbonyl" means "C=O."

In one embodiment of the invention, $R^1$ is selected from —$C_{1-10}$ alkyl, —$C_{0-10}$ alkylaryl, —$C_{0-10}$ alkylheterocyclyl, —$C_{0-10}$ alkyl-$C_{3-10}$cycloalkyl, and perfluoro$C_{1-6}$alkyl.

In a subset of this embodiment, $R^1$ is selected from —$C_{0-10}$ alkylaryl, and —$C_{0-10}$ alkylheterocyclyl.

In one embodiment of the invention, the aryl moiety in $R^1$, is selected from phenyl, naphthyl, tetrahydro-naphthyl, indanyl, 2,3-dihydro-1H-indenyl, or biphenyl.

In a subset of this embodiment, the aryl moiety in $R^1$, is selected from phenyl, biphenyl and -2,3-dihydroindenyl.

The heterocyclyl moiety in $R^1$, includes, but is not limited to, the following: azabenzimidazolyl, benzoimidazolyl, benzofuryl, benzofurazanyl, benzopyrazolyl, benzotriazolyl, benzothiophenyl, benzothiazolyl, benzothienyl, benzoxazolyl, carbazolyl, carbolinyl, chromanyl, cinnolinyl, furanyl, imidazolyl, indolinyl, indolyl, indolazinyl, indazolyl, isobenzofuryl, isochromanyl, isoindolyl, isoquinolyl, isothiazolyl, isoxazolyl, naphthpyridinyl, oxadiazolyl, oxazolyl, oxazolinyl, isoxazolinyl, oxetanyl, pyranyl, pyrazinyl, pyrazolyl, pyridazinyl, pyridopyridinyl, pyridazinyl, pyridinyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, aziridinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuryl, dihydrobenzothiophenyl, dihydrobenzoxazolyl, dihydrofuryl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, tetrahydroquinolinyl, tetrahydroisoquinolinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzyl, tetrahydrofuryl, tetrahydrothienyl, tetrahydroquinolinyl, 2,3-dihydrobenzofuryl, 2,3-dihydrobenzo-1,4-dioxinyl, imidazo(2,1-b)(1,3)thiazole, pyrimidinylphenyl, pyridinylphenyl, and benzo-1,3-dioxolyl.

In a variant of this embodiment, the heterocyclyl moiety in $R^1$ includes azabenzimidazolyl, benzoimidazolyl, benzofuryl, benzopyrazolyl, benzotriazolyl, benzothiophenyl, benzothiazolyl, benzothienyl, benzoxazolyl, carbazolyl, carbolinyl, furanyl, imidazolyl, indolinyl, indolyl, indolazinyl, indazolyl, isobenzofuryl, isoindolyl, isoquinolyl, isothiazolyl, isoxazolyl, naphthpyridinyl, oxadiazolyl, oxazolyl, oxazolinyl, isoxazolinyl, oxetanyl, pyranyl, pyrazinyl, pyrazolyl, pyridazinyl, pyridazinyl, pyridinyl, pyrimidyl, pyrrolyl, quinazolinyl, quinolyl, tetrahydropyranyl, tetrazolyl, thiadiazolyl, thiazolyl, thienyl, triazolyl, azetidinyl, piperazinyl, piperidinyl, pyrrolidinyl, morpholinyl, thiomorpholinyl, dihydrobenzoimidazolyl, methylenedioxybenzyl, tetrahydrofuryl, tetrahydrothienyl, tetrahydroquinolinyl, pyrimidinylphenyl, pyridinylphenyl.

In another embodiment, the heterocyclyl moiety in $R^1$ is selected from: pyridinyl, phenyl, thiazolyl, oxadiazolyl, benzothiazolyl, oxazolyl, quinolyl, benzothienyl, pyrazolyl, pyrazinyl, and pyridinyl.

In one embodiment of the present invention, $R^1$ is selected from —$C_{1-3}$ alkylaryl, and —$C_{1-3}$ alkylheterocyclyl.

In one embodiment of the invention, $R^8$ is selected from hydrogen, and $C_{1-6}$ alkyl, optionally substituted with a hydroxy, —SH, —$NH_2$ or —$CO_2H$.

In a variant of this embodiment, $R^8$ is hydrogen.

In an embodiment of the present invention, $R^2$ and $R^3$ are each independently selected from hydrogen, and —$C_{1-10}$ alkyl, wherein $C_{1-10}$ alkyl is unsubstituted or substituted with one or more fluorine atoms, and phenyl is unsubstituted or substituted with or more substituents selected from fluoro, chloro, hydroxyl, $C_{1-10}$ alkyl, and —$OC_{1-10}$ alkyl.

In a subset of this embodiment, $R^2$ and $R^3$ are each hydrogen.

In one embodiment, $R^4$, $R^5$, $R^6$, and $R^7$ are independently selected from hydrogen, —$C_1$-$C_{10}$ alkyl, ($C_{0-10}$ alkyl)aryl, ($C_{0-10}$ alkyl)heterocyclyl, wherein said alkyl, aryl, and heterocyclyl are optionally substituted by one or more substituents $R^9$ In a subset of the above-mentioned embodiment, $R^4$, $R^5$, $R^6$, and $R^7$ are each hydrogen.

Structural representations of compounds having substituents terminating with a methyl group may display the terminal methyl group either using the characters "$CH_3$", e.g. "—$CH_3$" or using a straight line representing the presence of the methyl group, e.g. "—", i.e.,

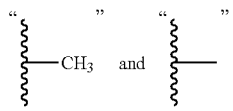

have equivalent meanings.

For variable definitions containing terms having repeated terms, e.g., $(CR^iR^j)_r$, where r is the integer 2, $R^i$ is a defined variable, and $R^j$ is a defined variable, the value of $R^i$ may differ in each instance in which it occurs, and the value of $R^j$ may differ in each instance in which it occurs. For example, if $R^i$ and $R^j$ are independently selected from the group consisting of methyl, ethyl, propyl and butyl, then $(CR^iR^j)_2$ can be

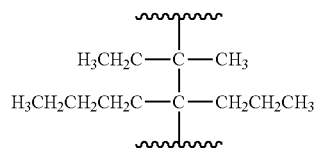

Optical Isomers—Diastereomers—Geometric Isomers—Tautomers

Compounds described herein may contain an asymmetric center and may thus exist as enantiomers. Where the compounds according to the invention possess two or more asymmetric centers, they may additionally exist as diastereomers. The present invention includes all such possible stereoisomers as substantially pure resolved enantiomers, racemic mixtures thereof, as well as mixtures of diastereomers. The above Formula I is shown without a definitive stereochemistry at certain positions. The present invention includes all stereoisomers of Formula I and pharmaceutically acceptable salts and solvates thereof. Unless specifically mentioned otherwise, reference to one isomer applies to any of the possible isomers. Whenever the isomeric composition is unspecified, all possible isomers are included. Diastereoisomeric pairs of enantiomers may be separated by, for example, fractional crystallization from a suitable solvent, and the pair of enantiomers thus obtained may be separated into individual stereoisomers by conventional means, for example by the use of an optically active acid or base as a resolving agent or on a chiral HPLC column. Further, any enantiomer or diastereomer of a compound of the general Formula I may be obtained by stereospecific synthesis using optically pure starting materials or reagents of known configuration.

When compounds described herein contain olefinic double bonds, unless specified otherwise, such double bonds are meant to include both E and Z geometric isomers.

Some of the compounds described herein may exist with different points of attachment of hydrogen, referred to as tautomers. For example, compounds including carbonyl —$CH_2C(O)$— groups (keto forms) may undergo tautomerism to form hydroxyl —CH=C(OH)— groups (enol forms). Both keto and enol forms, individually as well as mixtures thereof, are included within the scope of the present invention.

Salts

Pharmaceutically acceptable salts include both the metallic (inorganic) salts and organic salts; a list of which is given in *Remington's Pharmaceutical Sciences*, 17th Edition, pg. 1418 (1985). It is well known to one skilled in the art that an appropriate salt form is chosen based on physical and chemical stability, flowability, hydro-scopicity and solubility. As will be The term "pharmaceutically acceptable salts" refers to salts prepared from pharmaceutically acceptable non-toxic bases or acids. When the compound of the present invention is acidic, its corresponding salt can be conveniently prepared from inorganic bases or organic bases. Salts derived from such inorganic bases include aluminum, ammonium, calcium, copper (ic and ous), ferric, ferrous, lithium, magnesium, manganese (ic and ous), potassium, sodium, zinc and the like salts. Preferred are the ammonium, calcium, magnesium, potassium and sodium salts. Salts prepared from organic bases include salts of primary, secondary, and tertiary amines derived from both naturally occurring and synthetic sources. Pharmaceutically acceptable organic non-toxic bases from which salts can be formed include, for example, arginine, betaine, caffeine, choline, N,N'-dibenzylethylenediamine, diethylamine, 2-diethylaminoethanol, 2-dimethylamino-ethanol, ethanolamine, ethylenediamine, N-ethylmorpholine, N-ethylpiperidine, glucamine, glucosamine, histidine, hydrabamine, isopropylamine, dicyclohexylamine, lysine, methyl-glucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from inorganic or organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methane-sulfonic, mucic, nitric, pamoic, pantothenic, phosphoric, succinic, sulfuric, tartaric, p-toluene-sulfonic acid and the like. Preferred are citric, hydrobromic, hydrochloric, maleic, phosphoric, sulfuric, and tartaric acids.

Solvates

The present invention includes within its scope solvates of compounds of Formula I. As used herein, the term "solvate" refers to a complex of variable stoichiometry formed by a solute (i.e., a compound of Formula I) or a pharmaceutically acceptable salt thereof and a solvent that does not interfere with the biological activity of the solute. Examples of solvents include, but are not limited to water, ethanol, and acetic acid. When the solvent is water, the solvate is known as hydrate; hydrate includes, but is not limited to, hemi-, mono-, sesqui-, di- and trihydrates.

Prodrugs

The present invention includes within its scope the use of prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with a compound of formula I or with a compound which may not be a compound of formula I, but which converts to a compound of formula I in vivo after administration to the patient. Conventional procedures for the selection and preparation of suitable prodrug derivatives are described, for example, in "Design of Prodrugs," ed. H. Bundgaard, Elsevier, 1985.

Utilities

Compounds of the present invention are inhibitors of hypoxia-inducible factor (HIF) prolyl hydroxylases, and as such are useful in the treatment and prevention of diseases and conditions in which HIF modulation is desirable, such as anemia and ischemia. Compounds of the invention can be used in a selective and controlled manner to induce hypoxia-inducible factor stabilization and to rapidly and reversibly stimulate erythropoietin production and secretion. Accordingly, another aspect of the present invention provides a method of treating or preventing a disease or condition in a mammal, the treatment or prevention of which is effected or facilitated by HIF prolyl hydroxylase inhibition, which comprises administering an amount of a compound of Formula I that is effective for inhibiting HIF prolyl hydroxylase. This aspect of the present invention further includes the use of a compound of Formula I in the manufacture of a medicament for the treatment or prevention of a disease or condition modulated by HIF prolyl hydroxylase.

In one embodiment is a method of enhancing endogenous production of erythropoietin in a mammal which comprises administering to said mammal an amount of a compound of Formula I that is effective for enhancing endogenous production of erythropoietin.

Another embodiment is a method of treating anemia in a mammal which comprises administering to said mammal a therapeutically effective amount of a compound of Formula I. "Anemia" includes, but is not limited to, chronic kidney disease anemia, chemotherapy-induced anemia (e.g., anemia resulting from antiviral drug regimens for infectious diseases, such as HIV and hepatitis C virus), anemia of chronic disease, anemia associated with cancer conditions, anemia resulting from radiation treatment for cancer, anemias of chronic immune disorders such as rheumatoid arthritis, inflammatory bowel disease, and lupus, and anemias due to menstruation or of senescence or in other individuals with iron processing deficiencies such as those who are iron-replete but unable to utilize iron properly.

Another embodiment is a method of treating ischemic diseases in a mammal, which comprises administering to said mammal a therapeutically effective amount of a compound of Formula I.

Combination Therapy

Compounds of Formula I may be used in combination with other drugs that are used in the treatment/prevention/suppression or amelioration of the diseases or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical composition containing such other drugs in addition to the compound of Formula I is preferred. Accordingly, the pharmaceutical compositions of the present invention include those that also contain one or more other active ingredients, in addition to a compound of Formula I.

Route of Administration/Dosage

The compounds of this invention can be administered for the treatment or prevention of afflictions, diseases and illnesses according to the invention by any means that effects contact of the active ingredient compound with the site of action in the body of a warm-blooded animal. For example, administration can be oral, topical, including transdermal, ocular, buccal, intranasal, inhalation, intravaginal, rectal, intracisternal and parenteral. The term "parenteral" as used herein refers to modes of administration which include subcutaneous, intravenous, intramuscular, intraarticular injection or infusion, intrasternal and intraperitoneal. For the purpose of this disclosure, a warm-blooded animal is a member of the animal kingdom possessed of a homeostatic mechanism and includes mammals and birds.

The compounds can be administered by any conventional means available for use in conjunction with pharmaceuticals, either as individual therapeutic agents or in a combination of therapeutic agents. They can be administered alone, but are generally administered with a pharmaceutical carrier selected on the basis of the chosen route of administration and standard pharmaceutical practice.

The dosage administered will be dependent on the age, health and weight of the recipient, the extent of disease, kind of concurrent treatment, if any, frequency of treatment and the nature of the effect desired. Usually, a daily dosage of active ingredient compound will be from about 0.1-2000 milligrams per day. Ordinarily, from 10 to 500 milligrams per day in one or more applications is effective to obtain desired results. These dosages are the effective amounts for the treatment and prevention of afflictions, diseases and illnesses described above, e.g., anemia.

Pharmaceutical Composition

Another aspect of the present invention provides pharmaceutical compositions which comprises a compound of Formula I and a pharmaceutically acceptable carrier. The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula I, additional active ingredient(s), and pharmaceutically acceptable excipients.

The pharmaceutical compositions of the present invention comprise a compound represented by Formula I (or a pharmaceutically acceptable salt or solvate thereof) as an active ingredient, a pharmaceutically acceptable carrier and optionally other therapeutic ingredients or adjuvants. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

The active ingredient can be administered orally in solid dosage forms, such as capsules, tablets, troches, dragées, granules and powders, or in liquid dosage forms, such as elixirs, syrups, emulsions, dispersions, and suspensions. The active ingredient can also be administered parenterally, in sterile liquid dosage forms, such as dispersions, suspensions or solutions. Other dosages forms that can also be used to administer the active ingredient as an ointment, cream, drops, transdermal patch or powder for topical administration, as an ophthalmic solution or suspension formation, i.e., eye drops, for ocular administration, as an aerosol spray or powder composition for inhalation or intranasal administration, or as a cream, ointment, spray or suppository for rectal or vaginal administration.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene gycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propylparaben, and chlorobutanol.

Suitable pharmaceutical carriers are described in *Remington's Pharmaceutical Sciences*, A. Osol, a standard reference text in this field.

For administration by inhalation, the compounds of the present invention may be conveniently delivered in the form of an aerosol spray presentation from pressurized packs or nebulisers. The compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of a compound of Formula I in suitable propellants, such as fluorocarbons or hydrocarbons.

For ocular administration, an ophthalmic preparation may be formulated with an appropriate weight percent solution or suspension of the compounds of Formula I in an appropriate ophthalmic vehicle, such that the compound is maintained in contact with the ocular surface for a sufficient time period to allow the compound to penetrate the corneal and internal regions of the eye.

Useful pharmaceutical dosage-forms for administration of the compounds of this invention include, but are not limited to, hard and soft gelatin capsules, tablets, parenteral injectables, and oral suspensions.

A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

A mixture of active ingredient in a digestible oil such as soybean oil, cottonseed oil or olive oil is prepared and injected by means of a positive displacement pump into gelatin to form soft gelatin capsules containing 100 milligrams of the active ingredient. The capsules are washed and dried.

A large number of tablets are prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

A parenteral composition suitable for administration by injection is prepared by stirring 1.5% by weight of active ingredient in 10% by volume propylene glycol. The solution is made to volume with water for injection and sterilized.

An aqueous suspension is prepared for oral administration so that each 5 milliliters contain 100 milligrams of finely divided active ingredient, 100 milligrams of sodium carboxymethyl cellulose, 5 milligrams of sodium benzoate, 1.0 grams of sorbitol solution, U.S.P., and 0.025 milliliters of vanillin.

The same dosage forms can generally be used when the compounds of this invention are administered stepwise or in conjunction with another therapeutic agent. When drugs are administered in physical combination, the dosage form and administration route should be selected depending on the compatibility of the combined drugs. Thus the term coadministration is understood to include the administration of the two agents concomitantly or sequentially, or alternatively as a fixed dose combination of the two active components.

Compounds of the invention can be administered as the sole active ingredient or in combination with a second active ingredient, including other active ingredients known to be useful for improving the level of erythropoietin in a patient.

Abbreviations Used in the Description of the Preparation of the Compounds of the Present Invention:
AcOH Acetic acid
Aq Aqueous
Brine Saturated aqueous sodium chloride solution
$CH_2Cl_2$ Dichloromethane
DMF N,N-Dimethylformamide
Dppf 1,1"-bis(diphenylphosphino)ferrocene
DBU 1,8-diazabicyclo[5.4.0]undec-7-ene
DIEA N,N-diisopropylethylamine
DMAP 4-N,N-dimethylaminopyridine
DMF N,N-dimethylformamide
DMSO Dimethyl sulfoxide
EtOAc Ethyl acetate
EtOH Ethanol
$Et_2O$ or ether Diethyl ether
G grams
h or hr hour
HCl Hydrochloric acid
HPLC High-performance liquid chromatography
IPA 2-propanol
i-PrOH Isopropyl alcohol
Mg milligrams
mL milliliters
Mmol millimole
MeCN Acetonitrile
MeOH Methanol
Min minutes
ms or MS Mass pectrum
$Na_2SO_4$ Sodium sulfate
$R_f$ Retention time
Rt or r Room temperature
TFA Trifluoroacetic acid
THF tetrahydrofuran
µL microliters
Synthesis The compounds of this invention may be prepared by employing reactions as shown in the following schemes, in addition to other standard manipulations that are known in the literature or exemplified in the experimental procedures. The illustrative schemes below, therefore, are not limited by the compounds listed or by any particular substituents employed for illustrative purposes. Substituent numbering as shown in the schemes does not necessarily correlate to that used in the claims and often, for clarity, a single substituent is shown attached to the compound in place of multiple substituents which are allowed under the definitions of Formula I defined previously.

The following schemes and descriptions illustrate methods which may be employed for the synthesis of the novel compounds described in this invention. Two general subsets of compounds are described in this invention. The first subset consists of the N-[(4-hydroxy-1-methyl-2-oxo-1,2,5,7-tetrahydrothieno[3,4-b]pyridin-3-yl)carbonyl]glycines represented by structural formula Ia shown in Formula 1a-b. The second subset consists of the N-[7-hydroxy-4-methyl-5-oxo-2,3,4,5-tetrahydrothieno[3,2-b]pyridin-6-yl)carbonyl]glycines of formula 1b, also shown in Formula 1a-b. Several strategies based upon synthetic transformations known in the literature of organic synthesis may be employed for the preparation of the title compounds of general formulae Ia and Ib. Preferred synthetic processes, shown in the following reaction schemes begin with substituted alkyl oxotetrahydrothiophene-carboxylates of general formulae 1 and 9. In some cases, the alkyl oxotetrahydrothiophenecarboxylates (1 and 9) are commercially available; alternatively they may be synthesized using one of the methods illustrated in reaction schemes 3 and 4 respectively.

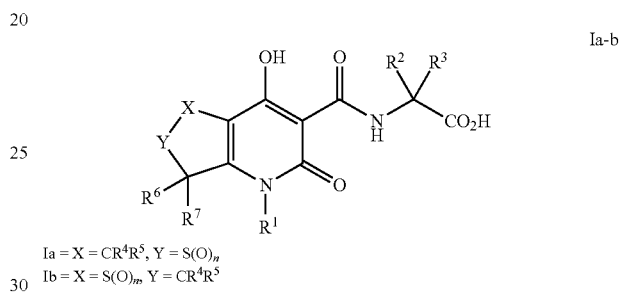

Ia = X = $CR^4R^5$, Y = $S(O)_n$
Ib = X = $S(O)_m$, Y = $CR^4R^5$

A preferred method for the synthesis of compounds of general formula Ia, representing the first subset of the compounds of this invention is presented in reaction Scheme 1, presented below.

Scheme 1

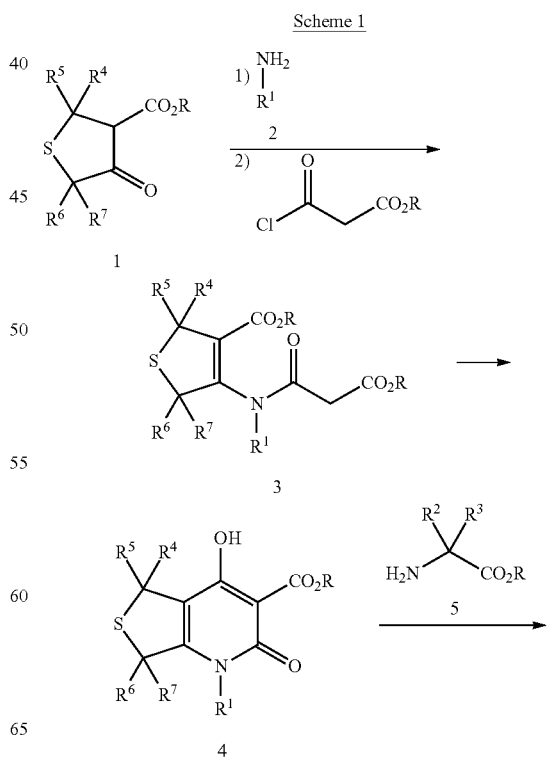

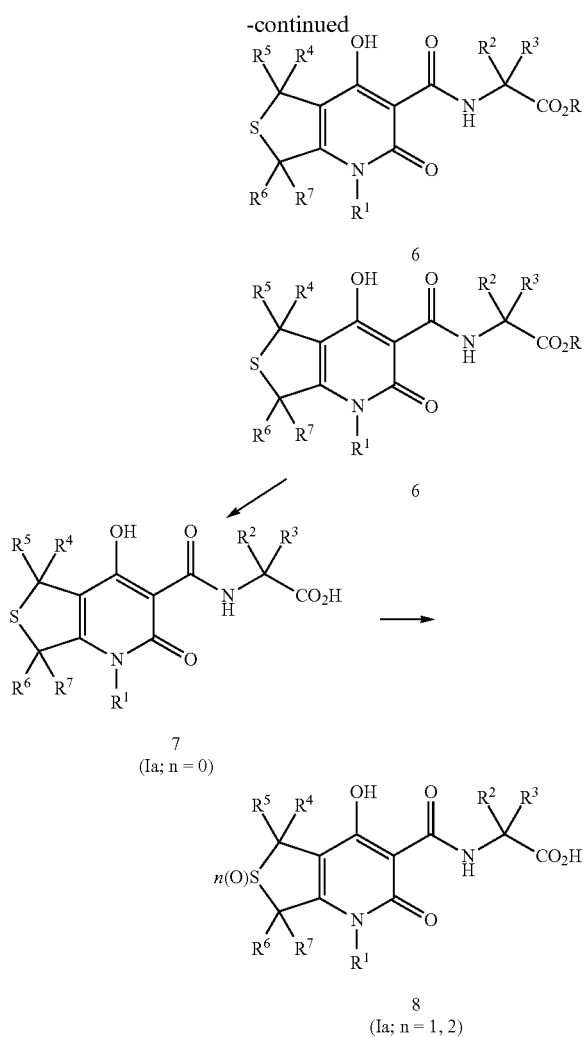

In this method, an alkyl 4-oxotetrahydrothiophene-3-carboxylate of general formula 1 is reacted with a primary amine of general formula 2 to provide a vinylogous amide which is subsequently acylated with methyl malonyl chloride to afford the substituted 2,5-dihydrothiophene-3-carboxylate derivative 3. The first step of this sequence is typically conducted in a solvent such as ethanol at elevated temperature, for instance at a temperature between about 50° C. and the refluxing temperature of ethanol, and the reaction is usually completed in about 1-24 hours. In some instances, formation of the vinylogous amide may be catalyzed by addition of several mole percent of acetic acid to the reaction mixture.

Alternatively, if the primary amine of general formula 2 is obtained in the form of a salt such as a hydrochloride salt, then an equivalent of a tertiary amine base such as triethylamine is typically added to the reaction mixture. After isolation the vinylogous amide is then treated with an aprotic solvent such as acetonitrile or the like, and acylated with methyl malonyl chloride. The acylation is conducted at temperatures between room temperature and approximately 65° C., and the reaction is generally complete in a period of 1-4 hours. The substituted 2,5-dihydrothiophene-3-carboxylate derivative 3 is then isolated using standard conditions for the workup and it may be purified by either chromatographic methods or by recrystallization.

The second step of the synthesis of the novel compounds of general formula Ia is an intramolecular Dieckmann reaction of a compound of general formula 3 to afford the alkyl 4-hydroxy-2-oxo-1,2,5,7-tetrahydrothieno[3,4-b]pyridine-3-carboxylate of general formula 4 as shown in reaction Scheme 1. This cyclization reaction is typically conducted using 1-2 equivalents of an alkali metal alkoxide as the base and the corresponding alcohol as solvent. The alcohol and the alkoxide employed are chosen to correspond to the alkyl substituent on the ester in the compound of general formula 4 to prevent the formation of mixtures of esters. The cyclization reaction is typically conducted at room temperature or slightly above room temperature and it generally proceeds to completion rapidly, for instance in 0.25 to 4 hours.

The next step in the synthesis of the compounds of general formula Ia is the conversion of the ester group of a compound of general formula 4 to the alkyl N-[(4-hydroxy-2-oxo-1,2,5,7-tetrahydrothieno[3,4-b]pyridin-3-yl)carbonyl]glycinate of general formula 6 as shown in reaction scheme 1. The transformation may be conducted by first hydrolyzing the ester at the 3-position to the corresponding carboxylic acid and then coupling it with a substituted glycine derivative of general formula 5 using standard amide bond coupling methods. A more preferred method for the conversion of 4 to 6 involves heating the ester 4 with the glycine derivative 5 in a suitable solvent which produces the amide 6 in a single step. This latter transformation is typically conducted in a solvent such as n-propanol at temperatures between 80 and 100° C. for periods of 1-5 hours.

The final step in the synthesis of the compounds of general formula Ia is the conversion of the glycine ester of the intermediate of general formula 6 to the corresponding carboxylic acid. The preferred method comprises selecting a glycine derivative of general formula 5 wherein the R group is a tent-butyl group. It is then possible to hydrolyze the glycinate of general formula 6 by treatment with an acid such as trifluoroacetic acid in a solvent like dichloromethane to afford a compound of general formula 7. This reaction is typically conducted at room temperature or slightly above room temperature and the reaction is usually complete in about 0.25-2 hours.

If the substituent R present in the ester of general formula 6 is methyl, ethyl or the like, then a standard hydrolysis reaction under basic conditions converts the ester 6 to the glycine derivative of general formula 7. Compounds of general formula 7 correspond to the title compounds of general formula Ia wherein n is equal to zero. When it is desired to prepare compounds of general formula Ia wherein n is equal to one or two (8), the compound of general formula 7 is subjected to oxidation with an oxidant such as magnesium bis(monoperoxyphthalate) (MMPP), m-chloroperoxybenzoic acid (MCPBA) or the like. These oxidation reactions are typically conducted at room temperature or below, using solvents such as dichloromethane or mixtures of dichloromethane and an alcohol.

A method for the synthesis of compounds of general formula Ib, representing the second subset of the compounds of this invention, is presented in reaction Scheme 2.

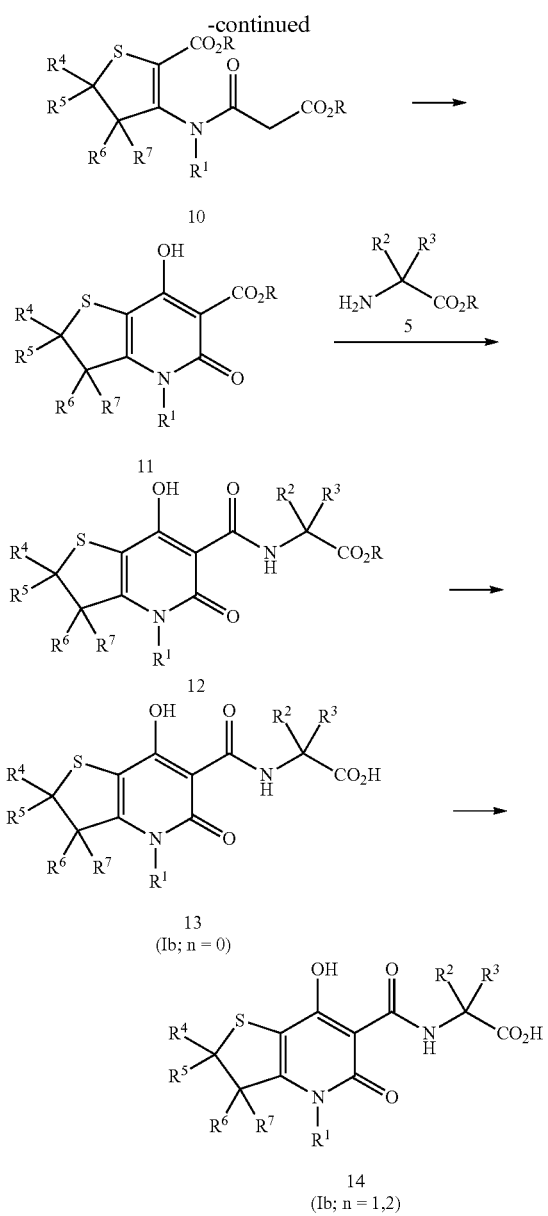

In this method, an alkyl 3-oxotetrahydrothiophene-2-carboxylate of general formula 9 is reacted with a primary amine of general formula 2 to provide a vinylogous amide which is subsequently acylated with methyl malonyl chloride to afford the substituted alkyl 4,5-dihydrothiophene-2-carboxylate derivative 10.

The first step of this sequence is typically conducted in a solvent such as ethanol at elevated temperature, for instance at a temperature between 50° C. and the refluxing temperature of ethanol, and the reaction is usually competed in about 1-24 hours. In some instances, formation of the vinylogous amide may be catalyzed by addition of several mole percent of acetic acid to the reaction mixture. Alternatively, if the primary amine of general formula 2 is obtained in the form of a salt such as a hydrochloride salt, then an equivalent of a tertiary amine base such as triethylamine is typically added to the reaction mixture.

After isolation the vinylogous amide is then treated to an aprotic solvent such as acetonitrile or the like, and acylated with methyl malonyl chloride. The acylation is conducted at temperatures between room temperature and approximately 65° C., and the reaction is generally complete in a period of 1-4 hours. The substituted alkyl 4,5-dihydrothiophene-2-carboxylate derivative 10 is then isolated using standard conditions for the workup and it may be purified by either chromatographic methods or by recrystallization.

The second step of the synthesis of the compounds of general formula Ib is an intramolecular Dieckmann reaction of a compound of general formula 10 to afford the alkyl 7-hydroxy-5-oxo-2,3,4,5-tetrahydrothieno[3,2-b]pyridine-6-carboxylate of general formula 11 as shown in reaction Scheme 2. This cyclization reaction is typically conducted using 1-2 equivalents of an alkali metal alkoxide as the base and the corresponding alcohol as solvent. The alcohol and the alkoxide employed are chosen to correspond to the alkyl substituent on the ester in the compound of general formula 10 to prevent the formation of mixtures of esters. The cyclization reaction is typically conducted at room temperature or slightly above room temperature and it generally proceeds to completion rapidly, for instance in 0.25 to 4 hours.

The next step in the synthesis of the novel compounds of general formula Ib is the conversion of the ester group of a compound of general formula 11 to the alkyl N-[(7-hydroxy-5-oxo-2,3,4,5-tetrahydrothieno[3,2-b]pyridin-6-yl)carbonyl]glycinate of general formula 12 as shown in reaction scheme 2. The transformation may be conducted by first hydrolyzing the ester at the 3-position to the corresponding carboxylic acid and then coupling it with a substituted glycine derivative of general formula 5 using standard amide bond coupling methods. A more preferred method for the conversion of 11 to 12 involves heating the ester 11 with the glycine derivative 5 in a suitable solvent which produces the amide 12 in a single step. This latter transformation is typically conducted in a solvent such as n-propanol at temperatures between 80 and 100° C. for periods of 1-5 hours.

The last step in the synthesis of the compounds of general formula Ib is the conversion of the glycine ester of the intermediate of general formula 12 to the corresponding carboxylic acid 13. One method of accomplishing this synthesis comprises selecting a glycine derivative of general formula 5 wherein the R group is a tert-butyl group. It is then possible to hydrolyze the glycinate of general formula 12 by treatment with an acid such as trifluoroacetic acid in a solvent like dichloromethane to afford a compound of general formula 13. This reaction is typically conducted at room temperature or slightly above room temperature and the reaction is usually complete in about 0.25-2 hours. If the substituent R present in the ester of general formula 12 is methyl, ethyl or the like, then a standard hydrolysis reaction under basic conditions converts the ester 12 to the glycine derivative of general formula 13.

Compounds of general formula 13 correspond to the title compounds of general formula Ib wherein n is equal to zero. When it is desired to prepare compounds of general formula Ib wherein n is equal to one or two (14), the compound of general formula 13 is subjected to oxidation with an oxidant such as magnesium bis(monoperoxyphthalate) (MMPP), m-chloroperoxybenzoic acid (MCPBA) or the like. These oxidation reactions are typically conducted at room temperature or below, using solvents such as dichloromethane or mixtures of dichloromethane and an alcohol.

As discussed previously, the substituted alkyl 4-oxotetrahydrothiophene-3-carboxylates of general formula 1 which are used as the starting material in reaction Scheme 1 may be commercially available. In instances when it is desired to employ an alkyl 4-oxotetrahydrothiophene-3-carboxylate of general formula 1 bearing substituents $R^4$ to $R^7$ which is not commercially available, these compounds may be prepared using methods known in the art of organic synthesis. For example, the Michael addition reaction of an α,β-unsaturated ester of general formula 15 with a substituted alkyl thioglycolate of general formula 16 affords a diester of general formula 17 as shown in reaction Scheme 3 (Woodward, R. B.; Eastman, R. H. *J. Amer. Chem. Soc.* 1946, 68, 2229-35). The diester of general formula 17 is then cyclized to alkyl 4-oxotetrahydrothiophene-3-carboxylate of general formula 1 using a Dieckmann reaction (Satoshi, T.; Ushirogochi, H.; Sano, S.; Nagao, Y. *Chem. Lett.* 1995, 4, 295-6).

Scheme 3

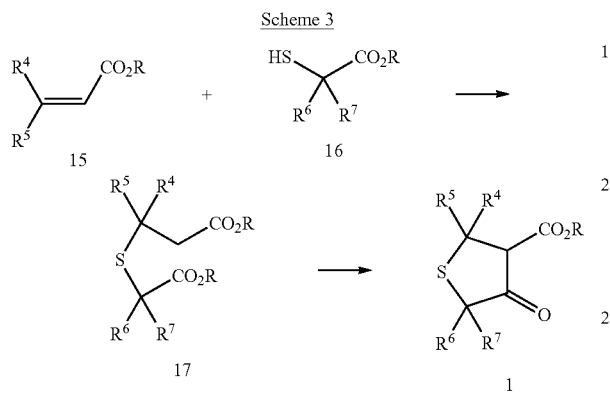

Similarly, the alkyl 3-oxotetrahydrothiophene-2-carboxylates of general formula 9 may be available commercially or they may be synthesized according to several methods published in the literature of organic synthesis such as the method illustrated in reaction Scheme 4.

Scheme 4

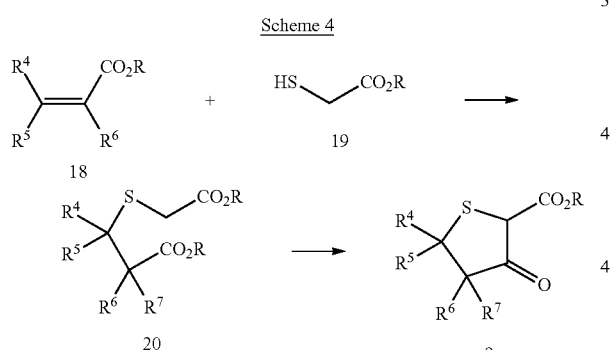

In this synthetic method, a modified Dieckmann reaction is also used to cyclize thioethers of general formula 20 to afford compounds of general formula 9 (Deshmukh, M. N.; Gangakhedkar, K. K.; Kumar, U. S. *Syn. Comm.* 1996, 26, 1657-61. Yamada, Y.; Ishii, T.; Kimura, M.; Hosaka, K. *Tetrahedron Lett.* 1981, 22, 1353-4). The thioethers of general formula 20 may in turn be prepared by a Michael addition of an alkyl thioglycolate of general formula 19 with α,β-unsaturated ester of general formula 18 (Struharik, M.; Hrnciar, P. *Chemical Papers* 1986, 40, 639-48. Woodward, R. B.; Eastman, R. H. *J. Am. Chem. Soc.* 1946, 68, 2229-35) or by other methods known in the literature of organic chemistry.

Finally, it is recognized that additional compounds of general formula Ia,b that are within the scope of this invention may be synthetically prepared using reactions known in the art of organic synthesis from one or more of the intermediate compounds shown as general formulae in reaction Schemes 1 and 2. For instance, one method embodies a cross-coupling reaction of an aryl or heterocyclyl ring incorporated in one of the substituent groups $R^1$ through $R^7$.

Reaction Scheme 5 illustrates examples wherein an aryl group present in the $R^1$ substituent of intermediates of general formulae 21a,b or 24a,b is reacted in a cross-coupling reaction with a suitable aryl or heterocyclyl organometallic reagent of general formula 22. The preferred cross-coupling reactions include Suzuki, Stille, Negishi and similar cross-coupling reactions known in the art of organic synthesis. In these examples the group X, and Y are as defined above, Z designates a suitable leaving group such as a halide atom or a triflate, the group M in the coupling partner 22 designates a stannane, boronic acid, boronate ester or the like, and the products of these reactions are the derivatives of general formulae 23a,b and 25a,b incorporating a biaryl element within the $R^1$ substituent. It is recognized that variants of the synthetic methods illustrated in reaction Scheme 5 are within the scope of this invention. For instance, one or both of the aryl groups in the newly formed biaryl element may be a heterocyclyl ring as defined above.

Scheme 3

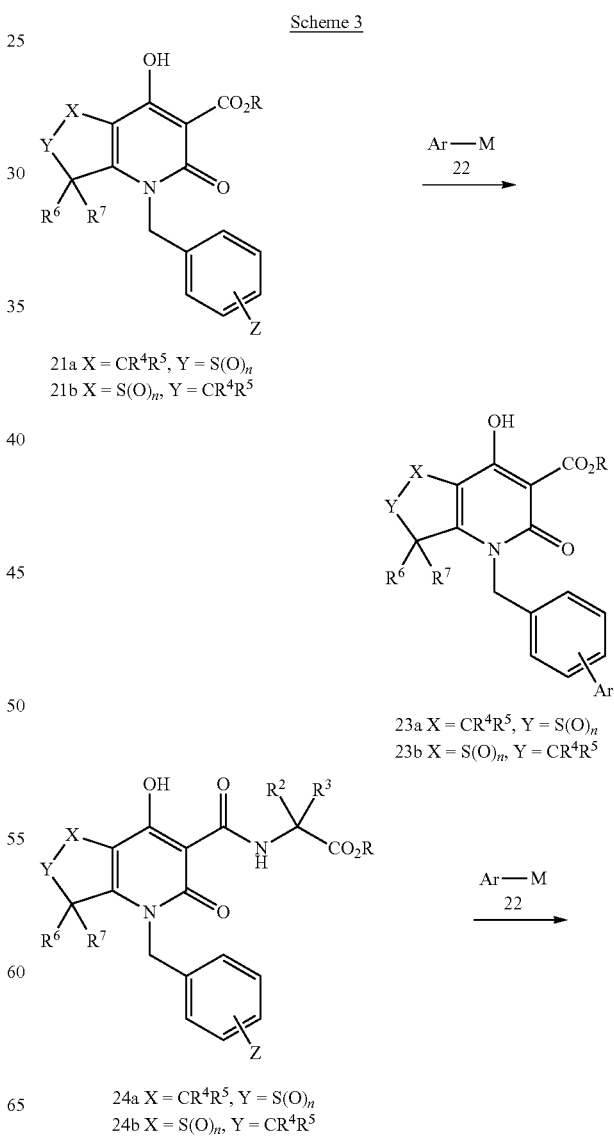

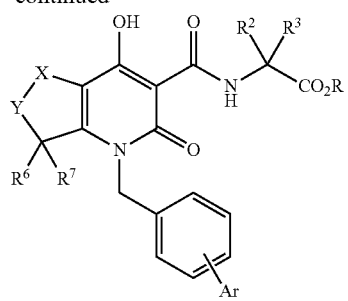

25a X = CR⁴R⁵, Y = S(O)$_n$
25b X = S(O)$_n$, Y = CR⁴R⁵

General Methods

Reactions sensitive to moisture or air were performed under nitrogen using anhydrous solvents and reagents. The progress of reactions was determined by either analytical thin layer chromatography (TLC) performed with E. Merck precoated TLC plates, silica gel 60F-254, layer thickness 0.25 mm or liquid chromatography-mass spectrum (LC-MS). Mass analysis was performed on a Waters Micromass® ZQ™ with electrospray ionization in positive ion detection mode. High performance liquid chromatography (HPLC) was conducted on an Agilent 1100 series HPLC on Waters C18 XTerra 3.5 μm 3.0×50 mm column with gradient 10:90-100 v/v CH$_3$CN/H$_2$O+v 0.05% TFA over 3.75 min then hold at 100 CH$_3$CN+v 0.05% TFA for 1.75 min; flow rate 1.0 mL/min, UV wavelength 254 nm). Concentration of solutions was carried out on a rotary evaporator under reduced pressure. Flash chromatography was performed using a Biotage Flash Chromatography apparatus (Dyax Corp.) on silica gel (32-63 mM, 60 Å pore size) in pre-packed cartridges.

Reference Example 1

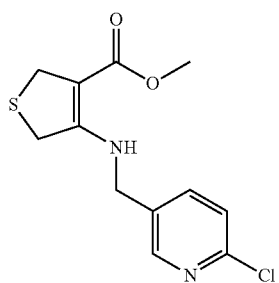

(RE-1)

Methyl 4-{[(6-chloropyridin-3-yl)methyl]amino}-2,5-dihydrothiophene-3-carboxylate (RE-1)

To methyl 4-oxo-tetrahydrothiophene-3-carboxylate (5.17 g, 32.3 mmol) in EtOH (69 mL) was added acetic acid (1.85 mL, 32.3 mmol). The reaction was heated at 80° C. overnight. The reaction was cooled, concentrated and then diluted with EtOAc. The solution was then washed with brine and aq Na$_2$CO$_3$ (2 M) (1:1) and then with brine. The solution was concentrated and the residue was purified by flash chromatography on silica gel gradient eluted with 0-40% EtOAc in hexane to afford the title compound (RE-1). HPLC/MS: 285.2 (M+1); R$_t$=2.84 min.

Reference Example 2

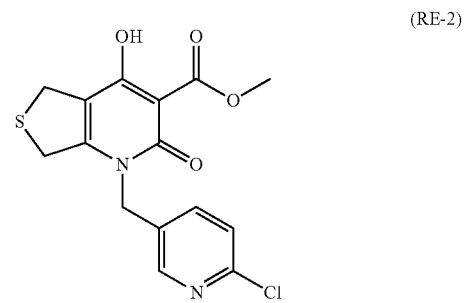 [SMILES: COC(=O)c1c(O)c2c(n(Cc3ccc(Cl)nc3)c1=O)CSC2]

(RE-2)

Methyl 1-[(6-chloropyridin-3-yl)methyl]-4-hydroxy-2-oxo-1,2,5,7-tetrahydrothieno[3,4-b]pyridine-3-carboxylate (RE-2)

Step A: Methyl 4-[[(6-chloropyridin-3-yl)methyl](3-methoxy-3-oxopropanoyl)amino]-2,5-dihydrothiophene-3-carboxylate To the product of Reference Example 1 (5.30 g 18.6 mmol) in MeCN, (20 mL) was added methyl 3-chloro-3-oxopropanoate (3.59 mL, 33.5 mmol) The mixture was stirred 90 min at 54° C. An additional portion of methyl 3-chloro-3-oxopropanoate (1 mL, 9.32 mmol) was added and then the reaction was heated to 65° C. for an additional 3.5 h. The reaction was concentrated and then diluted with EtOAc, washed with saturated aq NaHCO$_3$, brine, dried (Na$_2$SO$_4$), filtered and concentrated. The residue was purified by flash chromatography on silica gel gradient eluted with 0-100% EtOAc in hexane affording the product.

Step B: Methyl 1-[(6-chloropyridin-3-yl)methyl]-4-hydroxy-2-oxo-1,2,5,7-tetrahydrothieno[3,4-b]pyridine-3-carboxylate (RE-2)

To the product of Step A (6.645 g, 17.3 mol) in MeOH (60 mL) was added sodiummethoxide (5.92 mL, 25.9 mmol, 25 wt %) at rt. After 20 min the reaction was concentrated and then diluted with EtOAc and washed with aq HCl (2M) and then water providing the unpurified title compound (RE-2) which was used directly in Reference Example 3. HPLC/MS: 353.0 (M+1); R$_t$=2.68 min.

Reference Example 3

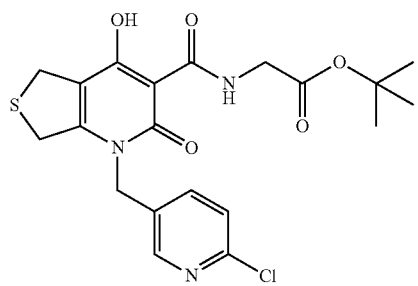 [SMILES: CC(C)(C)OC(=O)CNC(=O)c1c(O)c2c(n(Cc3ccc(Cl)nc3)c1=O)CSC2]

tert-Butyl N-({1-[(6-chloropyridin-3-yl)methyl]-4-hydroxy-2-oxo-1,2,5,7-tetrahydrothieno[3,4-b]pyridin-3-yl}carbonyl)glycinate (RE-3)

To the product of Reference Example 2 (5.64 g, 16.0 mmol) in 1-propanol (55 mL) was added tert-butyl glycinate (3.93 mL, 28.8 mmol). The reaction was stirred at 102° C. for 75 min and then placed in a freezer (−18) for 2 days to crystallize. The mixture was concentrated and the product was suspended in i-PrOH and isolated by filtration. The product was dried and then diluted with $CH_2Cl_2$ (100 mL). The cloudy solution was filtered through Celite® and then partially concentrated to about 80 mL. The product was crystallized by adding about 100 mL i-PrOH. After 1 h at rt, the product was isolated by filtration and dried in vacuo to afford the title compound (RE-3). HPLC/MS: 452.0 (M+1); $R_f$=3.44 min.

Example 1

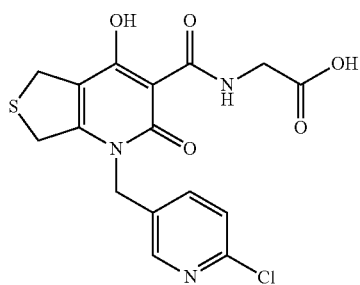

(1-1)

N-({1-[(6-chloropyridin-3-yl)methyl]-4-hydroxy-2-oxo-1,2,5,7-tetrahydrothieno[3,4-b]pyridin-3-yl}carbonyl)glycine (1-1)

To the product of Reference Example 3 (0.100 g, 0.221 mmol) was added $CH_2Cl_2$ (0.75 mL) and TFA (0.75 mL) at rt. After 1 hr the reaction was diluted with MeOH (5 mL) to crystallize the product. The mixture was concentrated and then diluted with MeOH. The crystals were isolated by filtration and washed twice with MeOH and once with hexane to afford the title compound. HPLC/MS: 396.0 (M+1); $R_f$=2.67 min.

Example 2

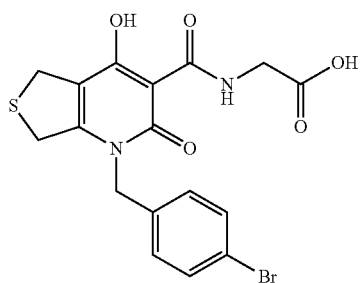

(2-1)

N-{([1-(4-bromobenzyl)-4-hydroxy-2-oxo-1,2,5,7-tetrahydrothieno[3,4-b]pyridin-3-yl]carbonyl}glycine (2-1)

To tert-butyl N-{[1-(4-bromobenzyl)-4-hydroxy-1,2,5,7-tetrahydrothieno[3,4-b]pyridin-3-yl]carbonyl}glycinate (prepared in similar fashion to Reference Example 3 and the preceding Reference Examples, 1.007 g, 2.033 mmol) was added $CH_2Cl_2$ (10.0 mL) and TFA (2.0 mL) at rt. After 1 hr the reaction was heated to 40° C. for an additional 4 h. The reaction was concentrated and then diluted with $Et_2O$ and MeOH to crystallize the sample. The liquid was decanted away and the solid was washed twice with hexane to afford the title compound. HPLC/MS: 438.9.0 (M+1); $R_f$=3.38 min.

Example 3

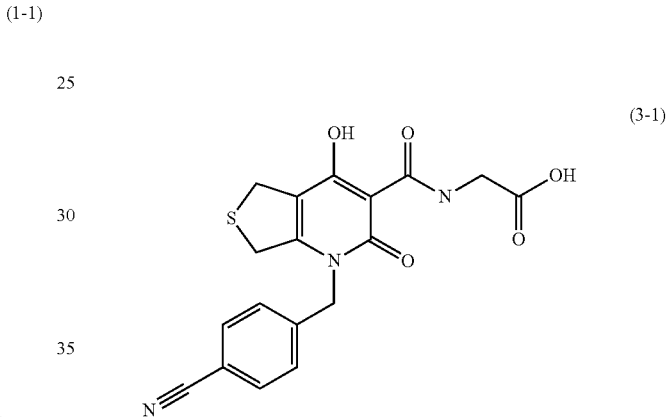

(3-1)

N-{[1-(4-cyanobenzyl)-4-hydroxy-2-oxo-1,2,5,7-tetrahydrothieno[3,4-b]pyridin-3-yl]carbonyl}glycine (3-1)

To the product of Example 3 (65 mg, 0.148 mmol) was added $Zn(CN)_2$ (17.4 mg, 0.148 mmol), tris(dibenzylideneacetone)dipalladium (0) (7.45 mg, 0.00814 mmol), 1,1'-bis(diphenylphosphino)ferrocene (10.8 mg, 0.020 mmol), DMF (2.0 mL) and water (0.2 mL). The reaction was purged with $N_2$ for 5 min at rt and then heated to 109° C. for about 4 h. The reaction was diluted with EtOAc, washed with brine/aq HCl (2 M) 1:1 and concentrated. The residue was purified by semi-preparative reverse phase HPLC on a C18 column, eluting with 15 to 100% $MeCN/H_2O$ (each containing 0.05% TFA) to afford the title compound (3-1). HPLC/MS: 386.0 (M+1); $R_f$=2.96 min.

Using procedures similar to that described in the Reference Examples and in Examples 1 and 2 coupled with the appropriate amine starting material, the compounds Examples 4 through 24 were prepared as shown in Table 1.

TABLE 1

| Example | Name | HPLC/MS m/z (M + 1) R_t (min) | Structure |
|---|---|---|---|
| Example 4 | N-({4-hydroxy-2-oxo-1-[4-(trifluoromethyl)benzyl]-1,2,5,7-tetrahydrothieno[3,4-b]pyridin-3-yl]carbonyl)glycine | 428.9 3.33 | 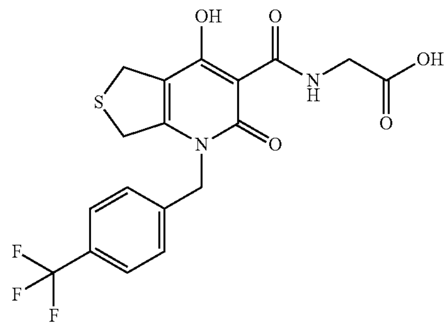 [SMILES: O=C(O)CNC(=O)c1c(O)c2c(n(Cc3ccc(C(F)(F)F)cc3)c1=O)CSC2] |
| Example 5 | N-[(4-hydroxy-2-oxo-1-{[6-(trifluoromethyl)pyridin-3-yl]methyl]-1,2,5,7-tetrahydrothieno[3,4-b]pyridin-3-yl)carbonyl]glycine | 429.9 2.81 | 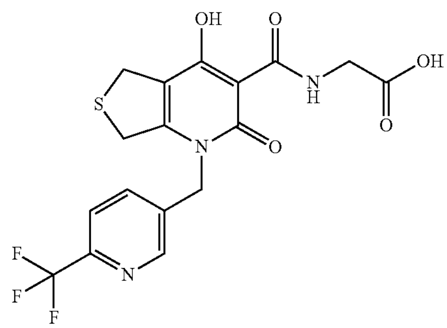 [SMILES: O=C(O)CNC(=O)c1c(O)c2c(n(Cc3ccc(C(F)(F)F)nc3)c1=O)CSC2] |
| Example 6 | N-({4-hydroxy-1-[4-(methylsulfonyl)benzyl]-2-oxo-1,2,5,7-tetrahydrothieno[3,4-d]pyridin-3-yl]carbonyl)glycine | 438.9 2.49 | 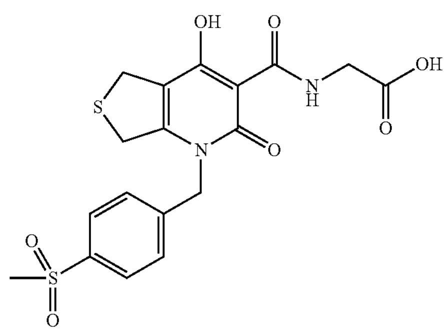 [SMILES: CS(=O)(=O)c1ccc(Cn2c3c(c(O)c(C(=O)NCC(=O)O)c2=O)CSC3)cc1] |
| Example 7 | N-({4-hydroxy-2-oxo-1-[(4-phenyl-1,3-thiazol-2-yl)methyl]-1,2,5,7-tetrahydrothieno[3,4-b]pyridin-3-yl}carbonyl)glycine | 443.9 3.24 | 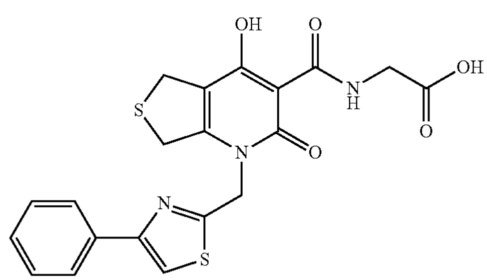 [SMILES: O=C(O)CNC(=O)c1c(O)c2c(n(Cc3nc(-c4ccccc4)cs3)c1=O)CSC2] |
| Example 8 | N-{[4-hydroxy-1-(4-isopropylbenzyl)-2-oxo-1,2,5,7-tetrahydrothieno[3,4-b]pyridin-3-yl]carbonyl}glycine | 403.1 3.35 | 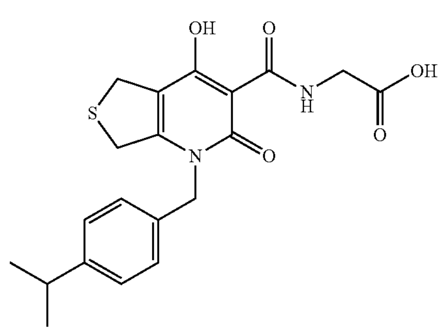 [SMILES: CC(C)c1ccc(Cn2c3c(c(O)c(C(=O)NCC(=O)O)c2=O)CSC3)cc1] |

TABLE 1-continued

| Example | Name | HPLC/MS m/z (M + 1) R$_t$ (min) | Structure |
|---|---|---|---|
| Example 9 | N-{[1-(4-tert-butylbenzyl)-4-hydroxy-2-oxo-1,2,5,7-tetrahydrothieno[3,4-b]pyridin-3-yl]carbonyl}glycine | 417.1 3.45 | 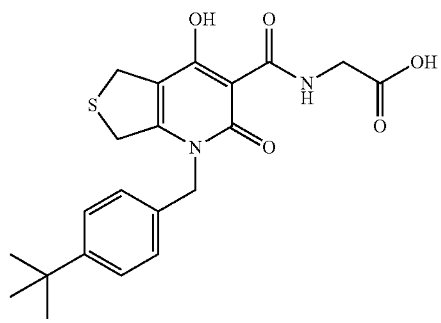 [SMILES: CC(C)(C)c1ccc(Cn2c3c(c(O)c(C(=O)NCC(=O)O)c2=O)CSC3)cc1] |
| Example 10 | N-({4-hydroxy-2-oxo-1-[(5-phenyl-1,2,4-oxadiazol-3-yl)methyl]-1,2,5,7-tetrahydrothieno[3,4-b]pyridin-3-yl}carbonyl)glycine | 429.0 2.97 | 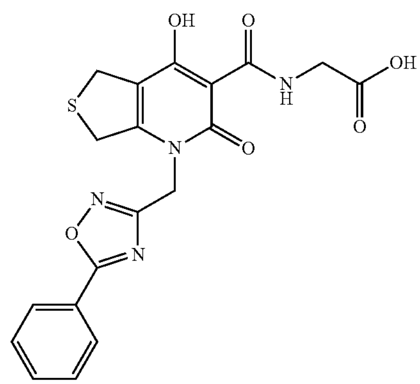 [SMILES: O=C(O)CNC(=O)c1c(O)c2c(n(Cc3noc(-c4ccccc4)n3)c1=O)CSC2] |
| Example 11 | N-{[1-(1,3-benzothiazol-2-ylmethyl)-4-hydroxy-2-oxo-1,2,5,7-tetrahydrothieno[3,4-b]pyridin-3-yl]carbonyl}glycine | 418.0 2.97 | 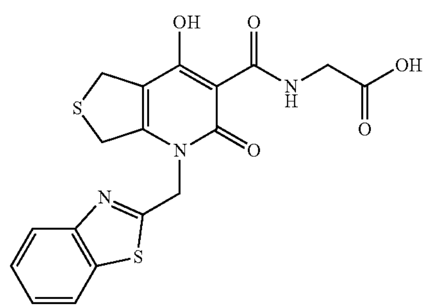 [SMILES: O=C(O)CNC(=O)c1c(O)c2c(n(Cc3nc4ccccc4s3)c1=O)CSC2] |
| Example 12 | N-{[1-(4-bromophenyl)-4-hydroxy-2-oxo-1,2,5,7-tetrahydrothieno[3,4-b]pyridin-3-yl]carbonyl}glycine | 424.9 2.94 | 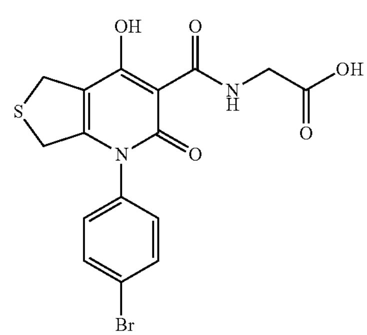 [SMILES: O=C(O)CNC(=O)c1c(O)c2c(n(-c3ccc(Br)cc3)c1=O)CSC2] |

TABLE 1-continued

| Example | Name | HPLC/MS m/z (M + 1) R$_t$ (min) | Structure |
|---|---|---|---|
| Example 13 | N-({1-[3-fluoro-5-(trifluoromethyl)benzyl]-4-hydroxy-2-oxo-1,2,5,7-tetrahydrothieno[3,4-b]pyridin-3-yl]carbonyl)glycine | 446.9 3.17 | 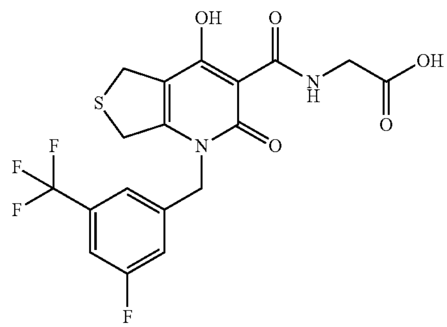 [SMILES: O=C(O)CNC(=O)c1c(O)c2c(n(Cc3cc(F)cc(C(F)(F)F)c3)c1=O)CSC2] |
| Example 14 | N-{[1-(3-chlorobenzyl)-4-hydroxy-2-oxo-1,2,5,7-tetrahydrothieno[3,4-b]pyridin-3-yl]carbonyl}glycine | 395.0 3.07 | 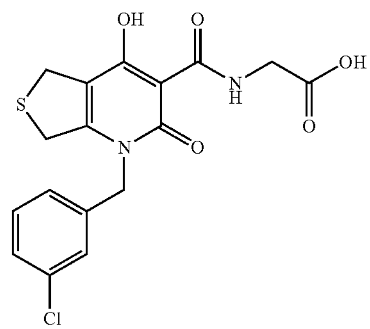 [SMILES: O=C(O)CNC(=O)c1c(O)c2c(n(Cc3cccc(Cl)c3)c1=O)CSC2] |
| Example 15 | N-{[1-(4-chloro-2-methylbenzyl)-4-hydroxy-2-oxo-1,2,5,7-tetrahydrothieno[3,4-b]pyridin-3-yl]carbonyl}glycine | 409.0 3.21 | 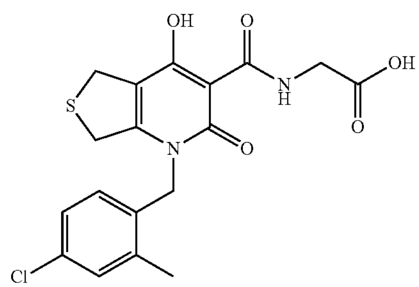 [SMILES: Cc1cc(Cl)ccc1Cn1c2c(c(O)c(C(=O)NCC(=O)O)c1=O)CSC2] |
| Example 16 | N-{[1-(4-chlorobenzyl)-4-hydroxy-2-oxo-1,2,5,7-tetrahydrothieno[3,4-b]pyridin-3-yl]carbonyl}glycine | 394.9 3.36 | 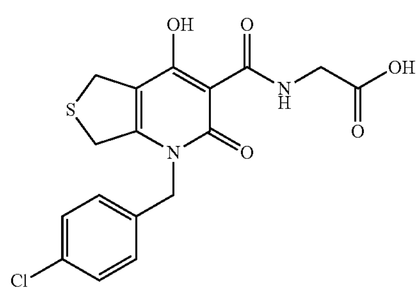 [SMILES: O=C(O)CNC(=O)c1c(O)c2c(n(Cc3ccc(Cl)cc3)c1=O)CSC2] |
| Example 17 | N-{[1-(4-ethylbenzyl)-4-hydroxy-2-oxo-1,2,5,7-tetrahydrothieno[3,4-b]pyridin-3-yl]carbonyl}glycine | 389.1 3.22 | 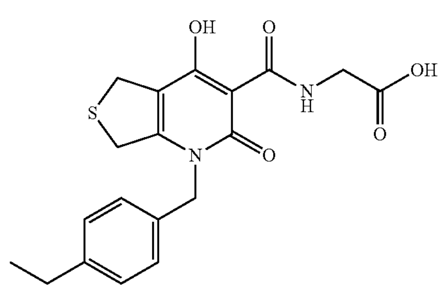 [SMILES: CCc1ccc(Cn2c3c(c(O)c(C(=O)NCC(=O)O)c2=O)CSC3)cc1] |

TABLE 1-continued

| Example | Name | HPLC/MS m/z (M + 1) R$_t$ (min) | Structure |
|---|---|---|---|
| Example 18 | N-({1-[4-chloro-3-(trifluoromethyl)benzyl]-4-hydroxy-2-oxo-1,2,5,7-tetrahydrothieno[3,4-b]pyridin-3-yl}carbonyl)glycine | 462.9 3.28 | 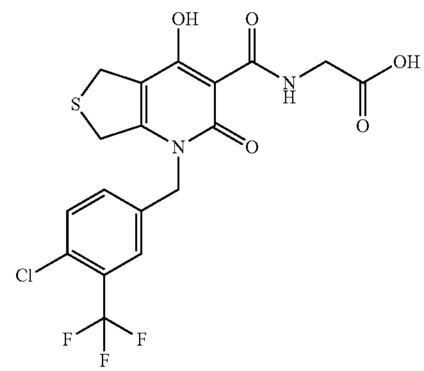 [SMILES: O=C(O)CNC(=O)c1c(O)c2c(n(Cc3ccc(Cl)c(C(F)(F)F)c3)c1=O)CSC2] |
| Example 19 | N-{[1-(3,4-dichlorobenzyl)-4-hydroxy-2-oxo-1,2,5,7-tetrahydrothieno[3,4-b]pyridin-3-yl]carbonyl}glycine | 428.9 3.26 | 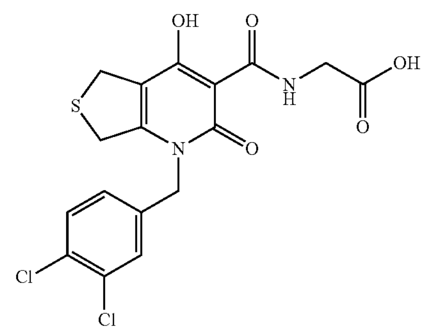 [SMILES: O=C(O)CNC(=O)c1c(O)c2c(n(Cc3ccc(Cl)c(Cl)c3)c1=O)CSC2] |
| Example 20 | N-({4-hydroxy-2-oxo-1-[4-(trifluoromethoxy)benzyl]-1,2,5,7-tetrahydrothieno[3,4-b]pyridin-3-yl}carbonyl)glycine | 445.0 3.24 | 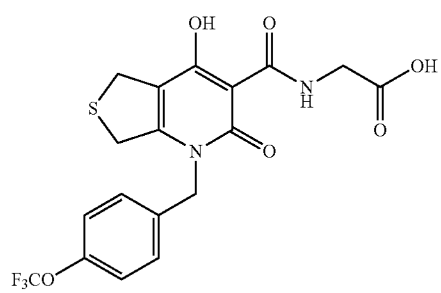 [SMILES: O=C(O)CNC(=O)c1c(O)c2c(n(Cc3ccc(OC(F)(F)F)cc3)c1=O)CSC2] |
| Example 21 | N-({4-hydroxy-2-oxo-1-[(2-phenyl-1,3-oxazol-4-yl)methyl]-1,2,5,7-tetrahydrothieno[3,4-b]pyridin-3-yl}carbonyl)glycine | 428.0 3.13 | 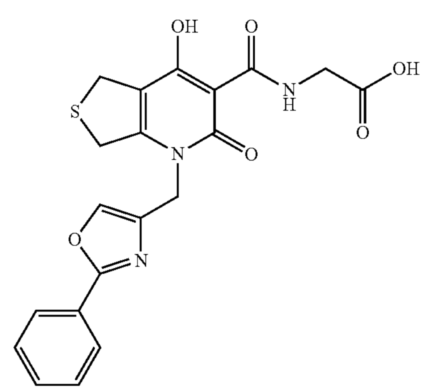 [SMILES: O=C(O)CNC(=O)c1c(O)c2c(n(Cc3coc(-c4ccccc4)n3)c1=O)CSC2] |

TABLE 1-continued

| Example | Name | HPLC/MS m/z (M + 1) $R_t$ (min) | Structure |
|---|---|---|---|
| Example 22 | N-{[1-(1-benzothien-2-ylmethyl)-4-hydroxy-2-oxo-1,2,5,7-tetrahydrothieno[3,4-b]pyridin-3-yl]carbonyl}glycine | 417.0<br>3.20 | 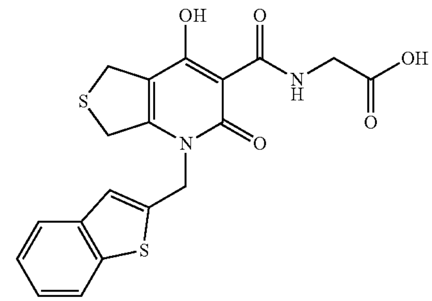 [SMILES: O=C(O)CNC(=O)c1c(O)c2c(n(Cc3cc4ccccc4s3)c1=O)CSC2] |
| Example 23 | N-({4-hydroxy-2-oxo-1-[4-(1H-pyrazol-1-yl)benzyl]-1,2,5,7-tetrahydrothieno[3,4-b]pyridin-3-yl}carbonyl)glycine | 427.1<br>2.87 | 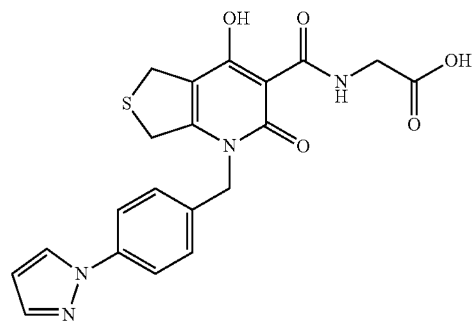 [SMILES: O=C(O)CNC(=O)c1c(O)c2c(n(Cc3ccc(-n4cccn4)cc3)c1=O)CSC2] |
| Example 24 | N-({4-hydroxy-2-oxo-1-[(1-phenyl-1H-pyrazol-4-yl)methyl]-1,2,5,7-tetrahydrothieno[3,4-b]pyridin-3-yl}carbonyl)glycine | 427.0<br>2.94 | 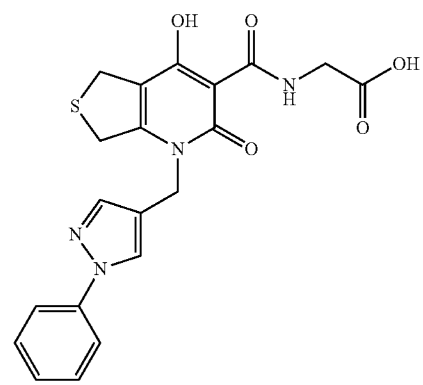 [SMILES: O=C(O)CNC(=O)c1c(O)c2c(n(Cc3cnn(-c4ccccc4)c3)c1=O)CSC2] |

Example 25

N-({4-hydroxy-1-[(4'-methylbiphenyl-4-yl)methyl]-2-oxo-1,2,5,7-tetrahydrothieno[3,4-b]pyridin-3-yl}carbonyl)glycine (25-1)

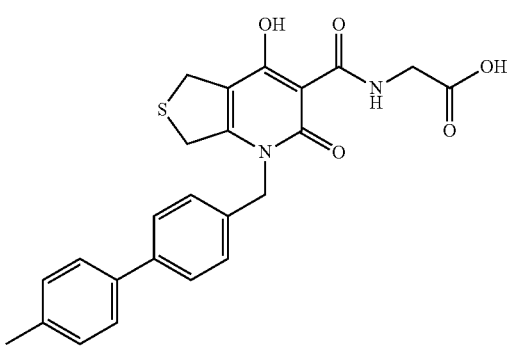

(25-1)

The product of Example 2 (2-1) (0.08 g, 0.16 mmol) was dissolved in DMA (2 mL) in a 10 mL reaction tube of a CEM Corporation Discover 300 Watt microwave reactor. An aq solution of $Na_2CO_3$ (2 M, 0.8 mL, 1.6 mmol), 4-tolylboronic acid (40 mg, 0.29 mmol) and bis(triphenylphosphine)palladium(II) chloride (11 mg, 0.016 mmol) were added and the tube was purged with nitrogen, capped and inserted into the microwave reactor. It was heated at 115° C., 50 watts maximum power, for 15 min. The reaction was diluted with EtOAc, washed with 2 M HCl, dried ($Na_2SO_4$), filtered and concentrated. The residue was purified by semi-preparative reverse phase HPLC on a C18 column eluted with 0-100% MeCN in water. The desired fractions were concentrated, dissolved in EtOAc and washed with water. The organic layer was dried ($Na_2SO_4$), filtered and concentrated affording the title compound (25-1). 450.9 (M+1); $R_t$=3.52 min.

Example 26

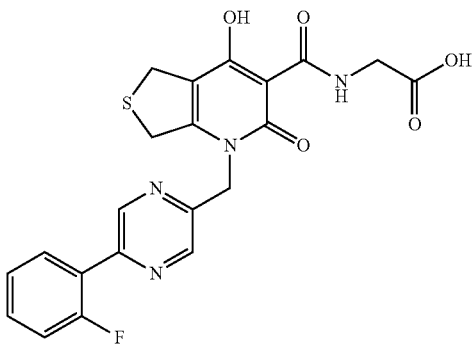

N-[(1-{[5-(2-fluorophenyl)pyrazin-2-yl]methyl}-4-hydroxy-2-oxo-1,2,5,7-tetrahydrothieno[3,4-b]pyridin-3-yl)carbonyl]glycine (26-1)

Step A: Tert-butyl N-[(1-{[5-(2-fluorophenyl)pyrazin-2-yl]methyl}-4-hydroxy-2-oxo-1,2,5,7-tetrahydrothieno[3,4-b]pyridin-3-yl)carbonyl]glycinate Tert-butyl N-[(1-{[5-(2-fluorophenyl)pyrazin-2-yl]methyl}-4-hydroxy-2-oxo-1,2,5,7-tetrahydrothieno[3,4-b]pyridin-3-yl)carbonyl]glycinate (prepared in similar fashion to Reference Example 3 and the preceding Reference Examples, 0.1 g, 0.22 mmol) was dissolved in DMA (1 mL) in a 10 mL reaction tube of a CEM Corporation Discover 300 Watt microwave reactor. An aq solution of $Na_2CO_3$ (2 M, 0.33 mL, 0.66 mmol), (2-fluorophenyl)boronic acid (56 mg, 0.4 mmol) and bis(triphenylphosphine)palladium(II) chloride (12 mg, 0.018 mmol) were added and the tube was purged with nitrogen, capped and inserted into the microwave reactor and heated at 110° C., 20 watts maximum power, for 12 min. The reaction was diluted with EtOAc, washed with 2 M HCl, dried ($Na_2SO_4$), filtered and concentrated. The residue was purified on a silica flash chromatography column eluted with 0-35% EtOAc in hexanes. The desired fractions were concentrated affording the compound. 513.1 (M+1); $R_t$=3.72 min.

Step B; N-[(1-{[5-(2-fluorophenyl)pyrazin-2-yl]methyl}-4-hydroxy-2-oxo-1,2,5,7-tetrahydrothieno[3,4-b]pyridin-3-yl)carbonyl]glycine (26-1)

Product of Step A (110 mg, 0.215 mmol) was dissolved in DCM (1 mL) and TFA (1 mL) was added. The reaction was stirred at ambient temperature for 3½h. The reaction was concentrated and the residue was purified on a semi-preparative C-18 reverse phase chromatography column eluted with 0-100% MeCN in water. The desired fractions were concentrated affording the title compound (26-1). 457.0 (M+1); $R_t$=3.09 min.

Using the general Suzuki coupling procedures described in Example 25 or Example 26 and the appropriate starting materials compounds Example 27 through Example 57 were obtained as shown in Table 2.

TABLE 2

| Example | Name | HPLC/MS m/z (M + 1) $R_t$ (min) | Structure |
|---|---|---|---|
| Example 27 | N-({4-hydroxy-2-oxo-1-[4-(1H-pyrazol-5-yl)benzyl]-1,2,5,7-tetrahydrothieno[3,4-b]pyridin-3-yl}carbonyl)glycine | 427.0 2.80 | 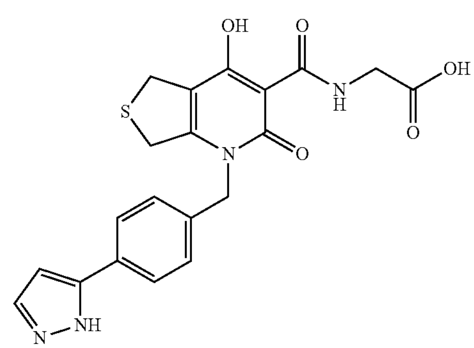 [SMILES: O=C(O)CNC(=O)c1c(O)c2c(n(Cc3ccc(-c4ccn[nH]4)cc3)c1=O)CSC2] |
| Example 28 | N-({1-[(4'-acetylbiphenyl-4-yl)methyl]-4-hydroxy-2-oxo-1,2,5,7-tetrahydrothieno[3,4-b]pyridin-3-yl}carbonyl)glycine | 479.0 3.40 | 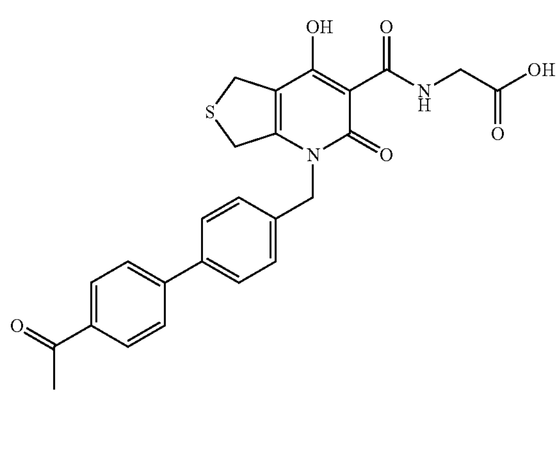 [SMILES: CC(=O)c1ccc(-c2ccc(Cn3c4c(c(O)c(C(=O)NCC(=O)O)c3=O)CSC4)cc2)cc1] |

TABLE 2-continued

| Example Name | HPLC/MS m/z (M + 1) R$_t$ (min) | Structure |
|---|---|---|
| Example 29 | N-{[1-(biphenyl-4-ylmethyl)-4-hydroxy-2-oxo-1,2,5,7-tetrahydrothieno[3,4-b]pyridin-3-yl]carbonyl}glycine | 436.9 3.38 | |
| Example 30 | N-({1-[(4'-chlorobiphenyl-4-yl)methyl]-4-hydroxy-2-oxo-1,2,5,7-tetrahydrothieno[3,4-b]pyridin-3-yl}carbonyl)glycine | 470.8 3.56 | |
| Example 31 | N-({1-[4-(3,5-dimethyl-1H-pyrazol-4-yl)benzyl]-4-hydroxy-2-oxo-1,2,5,7-tetrahydrothieno[3,4-b]pyridin-3-yl}carbonyl)glycine | 454.9 2.47 | |
| Example 32 | N-({1-[4-(4-fluorophenoxy)benzyl]-4-hydroxy-2-oxo-1,2,5,7-tetrahydrothieno[3,4-b]pyridin-3-yl}carbonyl)glycine | 471.3 3.74 | |

TABLE 2-continued

| Example Name | HPLC/MS m/z (M + 1) R$_t$ (min) | Structure |
|---|---|---|
| Example 33 | N-({1-[4-(4-chlorophenoxy)benzyl]-4-hydroxy-2-oxo-1,2,5,7-tetrahydrothieno[3,4-b]pyridin-3-yl}carbonyl)glycine | 487.0 3.91 | |
| Example 34 | N-({1-[(4'-ethoxybiphenyl-4-yl)methyl]-4-hydroxy-2-oxo-1,2,5,7-tetrahydrothieno[3,4-b]pyridin-3-yl}carbonyl)glycine | 481.1 3.48 | |
| Example 35 | N-({4-hydroxy-2-oxo-1-[4-(2-thienyl)benzyl]-1,2,5,7-tetrahydrothieno[3,4-b]pyridin-3-yl}carbonyl)glycine | 443.0 3.33 | |
| Example 36 | N-[(4-hydroxy-2-oxo-1-{[4'-(trifluoromethoxy)biphenyl-4-yl]methyl}-1,2,5,7-tetrahydrothieno[3,4-b]pyridin-3-yl)carbonyl]glycine | 521.3 3.69 | |

TABLE 2-continued

| Example | Name | HPLC/MS m/z (M + 1) R$_t$ (min) | Structure |
|---|---|---|---|
| Example 37 | N-{[1-({2'-[(diethylamino)carbonyl]biphenyl-4-yl}methyl)-4-hydroxy-2-oxo-1,2,5,7-tetrahydrothieno[3,4-b]pyridin-3-yl]carbonyl}glycine | 536.1 3.14 | 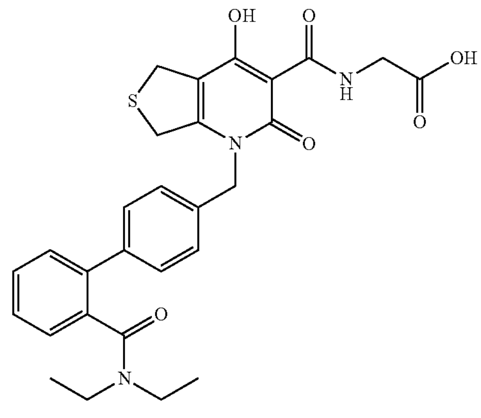 [SMILES: CCN(CC)C(=O)c1ccccc1-c1ccc(Cn2c3c(c(O)c(C(=O)NCC(=O)O)c2=O)CSC3)cc1] |
| Example 38 | N-({4-hydroxy-2-oxo-1-[4'-(trifluoromethoxy)biphenyl-4-yl]-1,2,5,7-tetrahydrothieno[3,4-b]pyridin-3-yl}carbonyl)glycine | 507.0 3.52 | 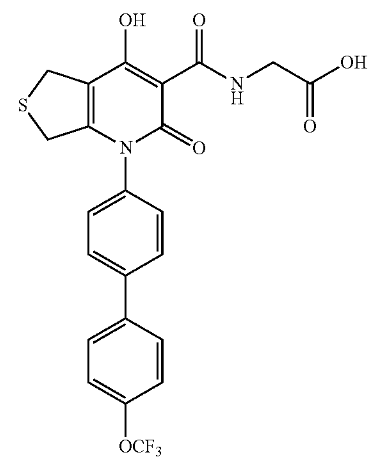 [SMILES: O=C(O)CNC(=O)c1c(O)c2c(n(-c3ccc(-c4ccc(OC(F)(F)F)cc4)cc3)c1=O)CSC2] |
| Example 39 | N-[(1-{[6-(3-chlorophenyl)pyridinium-3-yl]methyl}-4-hydroxy-2-oxo-1,2,5,7-tetrahydrothieno[3,4-b]pyridin-3-yl)carbonyl]glycine trifluoroacetate | 472.0 3.12 | 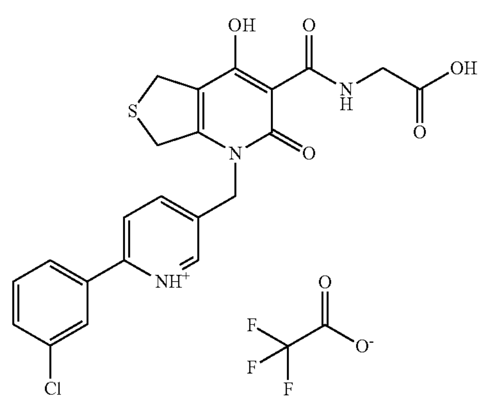 [SMILES: O=C(O)CNC(=O)c1c(O)c2c(n(Cc3ccc(-c4cccc(Cl)c4)[nH+]c3)c1=O)CSC2 ; O=C([O-])C(F)(F)F] |

TABLE 2-continued

| Example Name | HPLC/MS m/z (M + 1) R$_t$ (min) | Structure |
|---|---|---|
| Example 40 | N-[(1-{[6-(4-fluorophenyl)pyridinium-3-yl]methyl}-4-hydroxy-2-oxo-1,2,5,7-tetrahydrothieno[3,4-b]pyridin-3-yl)carbonyl]glycine trifluoroacetate | 456.0 2.77 | |
| Example 41 | N-[(1-{[6-(2-chlorophenyl)pyridinium-3-yl]methyl}-4-hydroxy-2-oxo-1,2,5,7-tetrahydrothieno[3,4-b]pyridin-3-yl)carbonyl]glycine trifluoroacetate | 472.0 2.83 | |
| Example 42 | N-({4-hydroxy-2-oxo-1-[3'-(trifluoromethoxy)biphenyl-4-yl]-1,2,5,7-tetrahydrothieno[3,4-b]pyridin-3-yl}carbonyl)glycine | 507.0 3.50 | |
| Example 43 | N-[(1-{[6-(2-fluorophenyl)pyridin-3-yl]methyl}-4-hydroxy-2-oxo-1,2,5,7-tetrahydrothieno[3,4-b]pyridin-3-yl)carbonyl]glycine | 456.0 2.77 | |

TABLE 2-continued

| Example Name | HPLC/MS m/z (M + 1) $R_t$ (min) | Structure |
|---|---|---|
| Example 44 | N-{[4-hydroxy-2-oxo-1-({6-[4-(trifluoromethyl)phenyl]pyridinium-3-yl}methyl)-1,2,5,7-tetrahydrothieno[3,4-b]pyridin-3-yl]caxbonyl}glycine trifluoroacetate | 506.0 3.25 | |
| Example 45 | N-{[4-hydroxy-2-oxo-1-({6-[2-(trifluoromethyl)phenyl]pyridinium-3-yl}methyl)-1,2,5,7-tetrahydrothieno[3,4-b]pyridin-3-yl]carbonyl}glycine trifluoroacetate | 506.0 2.97 | |
| Example 46 | N-({1-[(3'-cyanobiphenyl-4-yl)methyl]-4-hydroxy-2-oxo-1,2,5,7-tetrahydrothieno[3,4-b]pyridin-3-yl}carbonyl)glycine | 462.0 3.48 | |
| Example 47 | N-{[4-hydroxy-1-({6-[2-(methylthio)phenyl]pyridinium-3-yl}methyl)-2-oxo-1,2,5,7-tetrahydrothieno[3,4-b]pyridin-3-yl]carbonyl}glycine trifluoroacetate | 484.0 2.68 | |

TABLE 2-continued

| Example | Name | HPLC/MS m/z (M + 1) R$_t$ (min) | Structure |
|---|---|---|---|
| Example 48 | N-[(4-hydroxy-1-{[6-(2-methylphenyl)pyridinium-3-yl-methyl}-2-oxo-1,2,5,7-tetrahydrothieno[3,4-b]pyridin-3-yl)carbonyl]glycine trifluoroacetate | 452.1<br>2.50 | 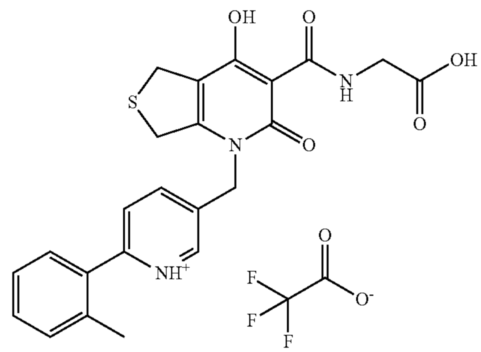 [SMILES: Cc1ccccc1-c1ccc(Cn2c3c(c(O)c(C(=O)NCC(=O)O)c2=O)CSC3)c[nH+]1 ; O=C([O-])C(F)(F)F] |
| Example 49 | N-{[4-hydroxy-2-oxo-1-({6-[3-(trifluoromethoxy)phenyl]pyridinium-3-yl}methyl)-1,2,5,7-tetrahydrothieno[3,4-b]pyridin-3-yl]carbonyl}glycine trifluoroacetate | 522.0<br>3.28 | 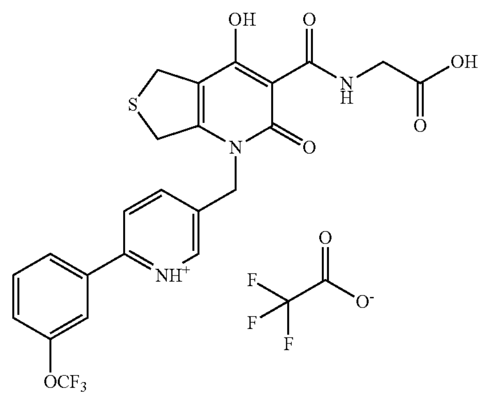 [SMILES: O=C(O)CNC(=O)c1c(O)c2c(n(Cc3ccc(-c4cccc(OC(F)(F)F)c4)[nH+]c3)c1=O)CSC2 ; O=C([O-])C(F)(F)F] |
| Example 50 | N-[(1-{[6-(2-ethylphenyl)pyridinium-3-yl]methyl}-4-hydroxy-2-oxo-1,2,5,7-tetrahydrothieno[3,4-b]pyridin-3-yl)carbonyl]glycine trifluoroacetate | 466.0<br>2.66 | 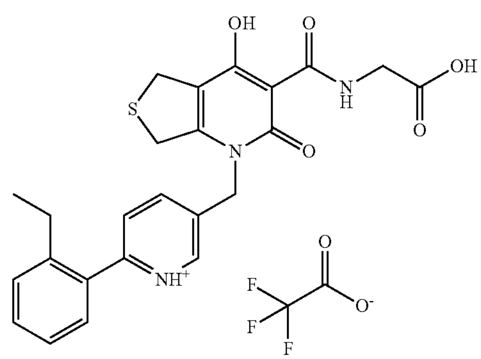 [SMILES: CCc1ccccc1-c1ccc(Cn2c3c(c(O)c(C(=O)NCC(=O)O)c2=O)CSC3)c[nH+]1 ; O=C([O-])C(F)(F)F] |
| Example 51 | N-[(1-{[6-(2,5-difluorophenyl)pyridinium-3-yl]methyl}-4-hydroxy-2-oxo-1,2,5,7-tetrahydrothieno[3,4-b]pyridin-3-yl)carbonyl]glycine trifluoroacetate | 474.1<br>3.04 | 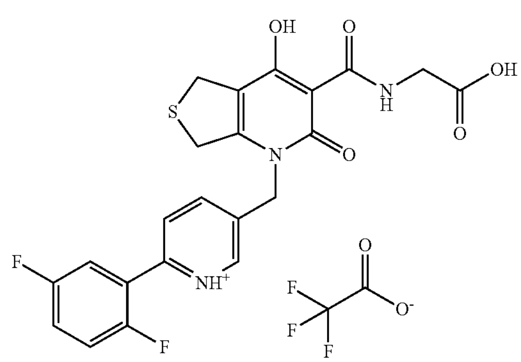 [SMILES: O=C(O)CNC(=O)c1c(O)c2c(n(Cc3ccc(-c4cc(F)ccc4F)[nH+]c3)c1=O)CSC2 ; O=C([O-])C(F)(F)F] |

TABLE 2-continued

| Example | Name | HPLC/MS m/z (M + 1) R$_t$ (min) | Structure |
|---|---|---|---|
| Example 52 | N-{[4-hydroxy-2-oxo-1-(4-quinolinium-5-ylbenzyl)-1,2,5,7-tetrahydrothieno[3,4-b]pyridin-3-yl]carbonyl}glycine chloride | 488.1 2.50 | 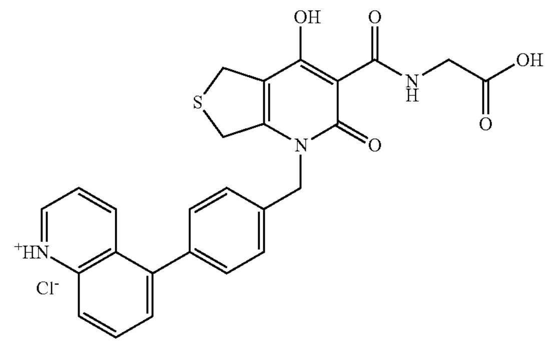 [SMILES: O=C(O)CNC(=O)c1c(O)c2c(n(Cc3ccc(-c4cccc5[nH+]cccc45)cc3)c1=O)CSC2 ; [Cl-]] |
| Example 53 | N-[(1-{[-5-(2-chlorophenyl)pyrazin-2-yl]methyl}-4-hydroxy-2-oxo-1,2,5,7-tetrahydrothieno[3,4-b]pyridin-3-yl)carbonyl]glycine | 473.0 3.75 | 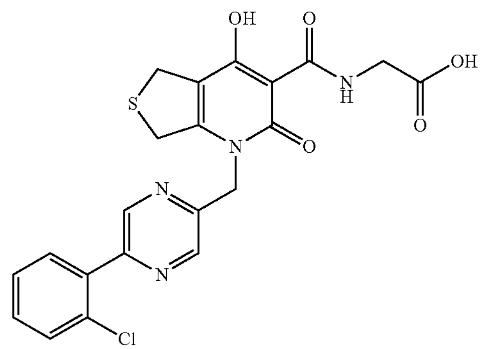 [SMILES: O=C(O)CNC(=O)c1c(O)c2c(n(Cc3cnc(-c4ccccc4Cl)cn3)c1=O)CSC2] |
| Example 54 | N-[(4-hydroxy-1-{[5-(2-methylphenyl)pyrazin-2-yl]methyl}-2-oxo-1,2,5,7-tetrahydrothieno[3,4-b]pyridin-3-yl)carbonyl]glycine | 453.0 3.10 | 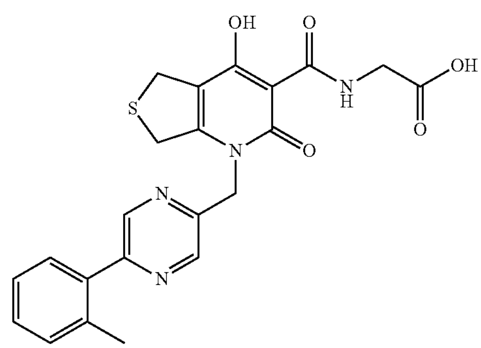 [SMILES: Cc1ccccc1-c1cnc(Cn2c3c(c(O)c(C(=O)NCC(=O)O)c2=O)CSC3)cn1] |
| Example 55 | N-{[4-hydroxy-1-({5-[2-(methylthio)phenyl]pyrazin-2-yl}methyl)-2-oxo-1,2,5,7-tetrahydrothieno[3,4-b]pyridin-3-yl]carbonyl}glycine | 485.0 3.11 | 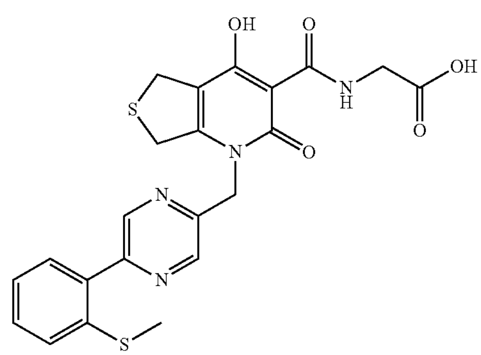 [SMILES: CSc1ccccc1-c1cnc(Cn2c3c(c(O)c(C(=O)NCC(=O)O)c2=O)CSC3)cn1] |

TABLE 2-continued

| Example Name | HPLC/MS m/z (M + 1) $R_t$ (min) | Structure |
|---|---|---|
| Example 56 N-[(1-{[5-(2,5-difluorophenyl)pyrazin-2-yl]methyl}-4-hydroxy-2-oxo-1,2,5,7-tetrahydrothieno[3,4-b]pyridin-3-yl)carbonyl]glycine | 475.0 3.14 | |
| Example 57 N-{[4-hydroxy-2-oxo-1-({5-[2-(trifluoromethyl)phenyl]pyrazin-2-yl}methyl)-1,2,5,7-tetrahydrothieno[3,4-b]pyridin-3-yl]carbonyl}glycine | 507.0 3.13 | |

Example 58

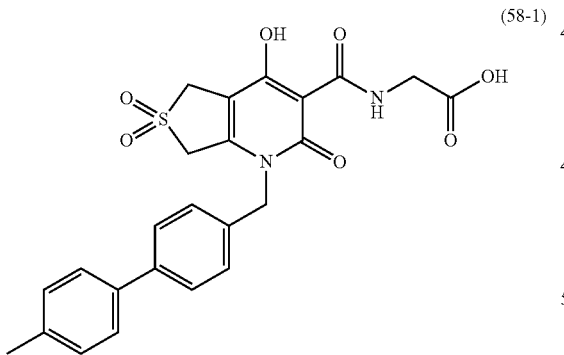

N-({4-hydroxy-1-[(4'-methylbiphenyl-4-yl)methyl]-6,6-dioxido-2-oxo-1,2,5,7-tetrahydrothieno[3,4-b]pyridin-3-yl}carbonyl)glycine (58-1)

The product of Example 25, (25-1), (36 mg, 0.08 mmol) was dissolved in DMF (1 mL) and mCPBA (41.2 mg, 0.184 mmol) was added. The reaction was heated at 35° C. for 5 h. The reaction was cooled and water (0.2 mL) was added. The reaction was filtered and purified by semi-preparative reverse phase HPLC on a C18 column eluted with 0-100% MeCN in water. Concentration of desired fractions afforded the product (58-1). HPLC/MS: 483.0 (M+1); $R_t$=3.12 min

Example 59

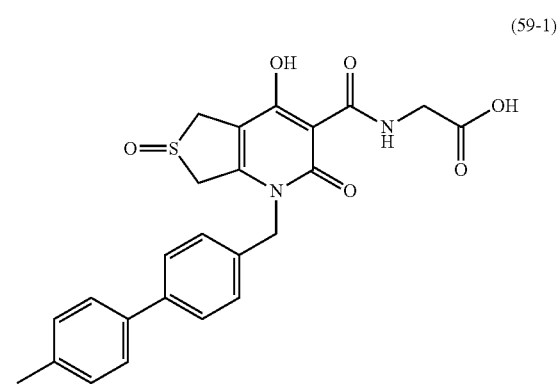 [SMILES: Cc1ccc(-c2ccc(Cn3c4c(c(O)c(C(=O)NCC(=O)O)c3=O)CS(=O)C4)cc2)cc1]

N-({4-hydroxy-1-[(4'-methylbiphenyl-4-yl)methyl]-6-oxido-2-oxo-1,2,5,7-tetrahydrothieno[3,4-b]pyridin-3-yl}carbonyl)glycine (59-1)

The title compound, (59-1) was isolated as a side product from Example 58 (58-1). HPLC/MS: 467.1 (M+1); $R_t$=2.90 min Using the procedure similar to that described in Example 58 and the appropriate sulfide compounds Example 60 through 66 were prepared as shown in Table 3.

TABLE 3

| Example Name | HPLC/MS m/z (M+1) Rt (min) | Structure |
| --- | --- | --- |
| Example 60 N-{[1-(4-chlorobenzyl)-4-hydroxy-6,6-dioxido-2-oxo-1,2,5,7-tetrahydrothieno[3,4-b]pyridin-3-yl]carbonyl}glycine | 426.9 2.65 | |
| Example 61 N-{[4-hydroxy-1-(4-isopropylbenzyl)-6,6-dioxido-2-oxo-1,2,5,7-tetrahydrothieno[3,4-b]pyridin-3-yl]carbonyl}glycine | 435.0 2.92 | |
| Example 62 N-({4-hydroxy-6,6-dioxido-2-oxo-1-[(4-phenyl-1,3-thiazol-2-yl)methyl]-1,2,5,7-tetrahydrothieno[3,4-b]pyridin-3-yl}carbonyl)glycine | 475.9 2.82 | |
| Example 63 N-({4-hydroxy-6,6-dioxido-2-oxo-1-[4-(trifluoromethyl)benzyl]-1,2,5,7-tetrahydrothieno[3,4-6]pyridin-3-yl}carbonyl)glycine | 461.0 2.76 | |
| Example 64 N-{[1-(biphenyl-4-ylmethyl)-4-hydroxy-6,6-dioxido-2-oxo-1,2,5,7-tetrahydrothieno[3,4-b]pyridin-3-yl]carbonyl}glycine | 469.0 2.98 | |

TABLE 3-continued

| Example | Name | HPLC/MS m/z (M+1) Rt (min) | Structure |
|---|---|---|---|
| Example 65 | N-({4-hydroxy-6,6-dioxido-2-oxo-1-[4-(trifluoromethoxy)benzyl]-1,2,5,7-tetrahydrothieno[3,4-b]pyridin-3-yl}carbonyl)glycine | 477.0 2.84 | 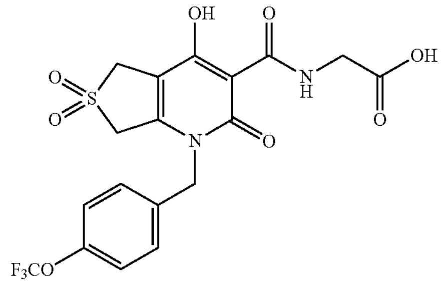 [SMILES: O=C(O)CNC(=O)c1c(O)c2c(n(Cc3ccc(OC(F)(F)F)cc3)c1=O)CS(=O)(=O)C2] |
| Example 66 | N-{[1-(4-ethylbenzyl)-4-hydroxy-6,6-dioxido-2-oxo-1,2,5,7-tetrahydrothieno[3,4-b]pyridin-3-yl]carbonyl}glycine | 421.0 2.78 | 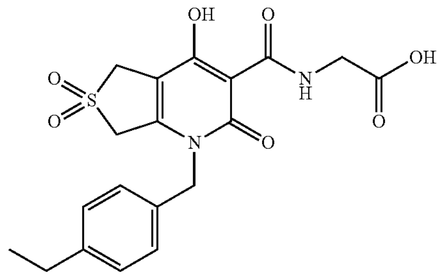 [SMILES: CCc1ccc(Cn2c3c(c(O)c(C(=O)NCC(=O)O)c2=O)CS(=O)(=O)C3)cc1] |

Biological Assays

The exemplified compounds, Examples 1 through 66, of the present invention, have been found to inhibit the interaction between PHD2 and HIF and exhibit $IC_{50}$ values ranging between 1 nanomolar to 10 micromolar. Non-limiting examples of assays that may be useful to detect favorable activity are disclosed in the following publications: Oehme, F., et al., *Anal. Biochem.* 330:74-80 (2004); Hirsilä, M, et al., *J. Bio. Chem.* 278 (33): 30772-30780 (2005); Hyunju, C., et al., *Biochem. Biophys. Res. Comm.* 330 (2005) 275-280; and Hewitson, K. S., et al., *Methods in Enzymology*, (Oxygen Biology and Hypoxia); Elsevier Publisher (2007), pg. 25-42 (ISSN: 0076-6879).

The biological activity of the present compounds may be evaluated using assays described herein below:

To each well of a 96-well plate was added 1 µL of test compound in DMSO and 20 µl of assay buffer (50 mM Tris pH 7.4/0.01% Tween-20/0.1 mg/ml bovine serum albumin/10 µM ferrous sulfate/1 mM sodium ascorbate/20 µg/ml catalase) containing 0.15 µg/ml FLAG-tagged full length PHD2 expressed in and purified from baculovirus-infected Sf9 cells. After a 30 min preincubation at room temperature, the enzymatic reactions were initiated by the addition of 4 µL of substrates (final concentrations of 0.2 µM 2-oxoglutarate and 0.5 µM HIF-1α peptide biotinyl-DLDLEMLAPYIPMD-DDFQL). After 2 hr at room temperature, the reactions were terminated and signals were developed by the addition of a 25 µL quench/detection mix to a final concentration of 1 mM ortho-phenanthroline, 0.1 mM EDTA, 0.5 nM anti-$(His)_6$ LANCE reagent (Perkin-Elmer Life Sciences), 100 nM AF647-labeled streptavidin (Invitrogen), and 2 µg/ml $(His)_6$-VHL complex (S. Tan (2001) Protein Expr. Purif 21, 224-234). The ratio of time resolved fluorescence signals at 665 and 620 nm was determined, and percent inhibition was calculated relative to an uninhibited control sample run in parallel.

Inhibition of the catalytic activity of HIF-PHD1 and HIF-PHD3 can be determined similarly.

Table 4 includes the PHD2 binding activity for Examples 1-66 expressed as $IC_{50}$ (nM):

TABLE 4

| Example | PHD2 Activity |
|---|---|
| 1 | + |
| 2 | + |
| 3 | + |
| 4 | + |
| 5 | + |
| 6 | + |
| 7 | + |
| 8 | + |
| 9 | + |
| 10 | + |
| 11 | + |
| 12 | + |
| 13 | ++ |
| 14 | + |
| 15 | + |
| 16 | + |
| 17 | + |
| 18 | + |
| 19 | + |
| 20 | + |
| 21 | + |
| 22 | + |
| 23 | + |
| 24 | + |
| 25 | + |
| 26 | + |
| 27 | + |
| 28 | + |
| 29 | + |
| 30 | + |
| 31 | + |
| 32 | + |
| 33 | + |
| 34 | + |
| 35 | + |

TABLE 4-continued

| Example | PHD2 Activity |
|---|---|
| 36 | + |
| 37 | + |
| 38 | ++ |
| 39 | + |
| 40 | + |
| 41 | + |
| 42 | + |
| 43 | + |
| 44 | + |
| 45 | + |
| 46 | + |
| 47 | + |
| 48 | + |
| 49 | + |
| 50 | + |
| 51 | + |
| 52 | + |
| 53 | + |
| 54 | + |
| 55 | + |
| 56 | + |
| 57 | + |
| 58 | + |
| 59 | + |
| 60 | + |
| 61 | + |
| 62 | ++ |
| 63 | + |
| 64 | + |
| 65 | + |
| 66 | + |

+ = ≦10 $IC_{50}$ (nM)
++ = >10 to ≦100 $IC_{50}$ (nM)

What is claimed is:

1. A compound of formula I and pharmaceutically acceptable salts thereof

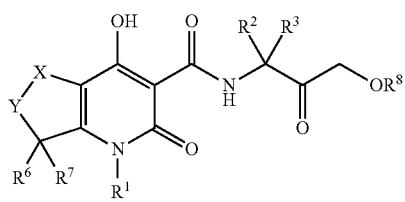

I wherein
$R^8$ is selected from hydrogen, $C_{1-6}$ alkyl, optionally substituted with a hydroxy, —SH, —NH$_2$ or —CO$_2$H, and $C_{3-6}$ cycloalkyl optionally substituted with a hydroxy, —SH, —NH$_2$ or —CO$_2$H;
n is 1 or 2;
one of X or Y is —S(O)$_n$, and the other is $CR^4R^5$;
$R^1$ is selected from
—$C_{1-10}$ alkyl,
—$C_{2-10}$ alkenyl,
—$C_{5-10}$ cycloalkenyl,
—$C_{2-10}$ alkynyl,
—$C_{0-10}$ alkylaryl,
—$C_{0-10}$ alkylheterocyclyl;
—$C_{0-10}$ alkyl-$C_{0-10}$ cycloalkyl, and perfluoro$C_{1-6}$alkyl;
wherein in $R^1$ said alkyl, alkenyl, alkynyl, cycloalkenyl, aryl, heterocycloalkyl, heterocyclyl, and cycloalkyl are each optionally substituted with one or more $R^9$ substituents;

$R^2$ and $R^3$ are independently selected from hydrogen, phenyl, heterocyclyl, and —$C_{1-10}$ alkyl, wherein $C_{1-10}$ alkyl is unsubstituted or substituted with one or more fluorine atoms, and phenyl is unsubstituted or substituted with or more substituents selected from fluoro, chloro, hydroxyl,
$C_{1-10}$ alkyl, and —OC$_{1-10}$ alkyl;
$R^4$, $R^5$, $R^6$, and $R^7$ are independently selected from hydrogen, cyano, oxo, —$C_1$-$C_{10}$ alkyl, —$C_{2-10}$ alkenyl, —$C_{3-10}$ cycloalkyl, —($C_{1-10}$ alkyl)aryl, ($C_{0-10}$ alkyl)heterocyclyl, —$C_{5-10}$ cycloalkenyl, —$C_{2-10}$ alkynyl, —SO$_n$($C_{1-10}$ alkyl) and —SO$_n$aryl wherein said alkyl, alkenyl, alkynyl, cycloalkyl, cycloalkenyl, aryl, and heterocyclyl are optionally substituted by one or more substituents $R^9$, and
optionally one set of substituents, $R^4$ and $R^5$, or $R^6$ and $R^7$, are linked together to form a ring of 5 to 8 atoms optionally substituted with one or more substituents $R^9$; where said ring is partially or fully unsaturated having 0, 1 or 2 heteroatoms independently selected from —NR$^6$—, —O— and —S(O)$_n$—;
$R^9$ is selected from halogen, hydroxy, oxo, cyano, aryl, heterocyclyl, —$C_{1-6}$ alkyl, —$C_{1-6}$ alkoxy, aryloxy, heterocyclyloxy, —CO$_2R^a$, —NR$^b$R$^c$, —CONR$^b$R$^c$, —OCO$_2R^a$, —OCONR$^b$R$^c$, —NR$^d$CO$_2R^a$, —NR$^d$CONR$^b$R$^c$, —SC$_{0-6}$ alkyl and —S(O)$_n$R$^d$, wherein said aryl, heterocyclyl, alkoxy, aryloxy, heterocyclyloxy are optionally substituted by one or more substituents $R^{10}$;
$R^{10}$ is selected from hydroxy, aryl, heterocyclyl, halogen, —$C_{1-6}$ alkyl, $C_{1-6}$ alkoxy, halogen, CO$_2$H, cyano, O(C═O)$_{0-1}$C$_{1-6}$ alkyl, NO$_2$, trifluoromethoxy, trifluoroethoxy, —O$_{(0-1)}$(C$_{1-10}$)perfluoroalkyl, C$_{0-10}$ alkylaminocarbonylamino, C$_{0-10}$ alkyloxycarbonylaminoC$_{0-10}$ alkyl, C$_{0-10}$ alkylcarbonylaminoC$_{0-10}$ alkyl, C$_{0-10}$ alkylaminosulfonylaminoC$_{0-10}$ alkyl, C$_{0-10}$ alkylsulfonylaminoC$_{0-10}$ alkyl, C$_{0-10}$ alkylsulfonyl, C$_{0-10}$ alkylaminosulfonyl, C$_{0-10}$ alkylaminocarbonyl, —(C═O)N(C$_{0-6}$ alkyl)$_2$, —S(C$_{0-6}$ alkyl), and NH$_2$;
$R^a$ is chosen from hydrogen; —$C_{1-10}$ alkyl, —(C$_{1-6}$ alkyl)C$_{3-8}$ cycloalkyl; and
—(C$_{1-6}$ alkyl)phenyl; and
$R^b$, $R^c$, and $R^d$ are each independently chosen from hydrogen, —$C_{1-10}$ alkyl, —$C_{3-10}$ cycloalkyl, aryl, and heterocyclyl, wherein said alkyl, cycloalkyl, aryl and heterocyclyl are optionally substituted by one or more substituents $R^{10}$.

2. A compound of claim 1 wherein X is —S(O)$_n$, and Y is $CR^4R^5$.

3. A compound of claim 1 wherein Y is —S(O)$_n$, and X is $CR^4R^5$.

4. A compound of claim 1 wherein $R^1$ is selected from —$C_{0-10}$ alkylaryl, and —$C_{0-10}$ alkylheterocyclyl.

5. A compound of claim 4, wherein $C_{0-10}$ alkylaryl is —$C_{1-3}$ alkylaryl and the aryl moiety is selected from phenyl, napthyl, tetrahydronaphthyl, indanyl, biphenyl and 2,3-dihydroindenyl.

6. A compound of claim 5 wherein —$C_{1-3}$ alkylaryl is selected from wherein —$C_{1-3}$ alkylphenyl, —$C_{1-3}$ alkybiphenyl and —$C_{1-3}$ alkybiphenyl 2,3-dihydroindenyl.

7. A compound of claim 4 wherein $R^1$ is —$C_{0-10}$ alkylheterocyclyl.

8. A compound of claim 7, wherein in —$C_{0-10}$ alkylheterocyclyl, the heterocyclyl moiety is selected from azabenzimidazolyl, benzoimidazolyl, benzofuryl, benzofurazanyl, benzopyrazolyl, benzotriazolyl, benzothiophenyl, benzothiazolyl, benzothienyl, benzoxazolyl, carbazolyl, carbolinyl, chromanyl, cinnolinyl, furanyl, imidazolyl, indolinyl, indolyl, indolazinyl, indazolyl, isobenzofuryl, isochromanyl, isoindolyl, isoquinolyl, isothiazolyl, isoxazolyl, naphthpyridinyl, oxadiazolyl, oxazolyl, oxazolinyl, isoxazolinyl, oxetanyl, pyranyl, pyrazinyl, pyrazolyl, pyridazinyl, pyridopyridinyl, pyridazinyl, pyridinyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, aziridinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuryl, dihydrobenzothiophenyl, dihydrobenzoxazolyl, dihydrofuryl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, tetrahydroquinolinyl, tetrahydroisoquinolinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzyl, tetrahydrofuryl, tetrahydrothienyl, tetrahydroquinolinyl, 2,3-dihydrobenzofuryl, 2,3-dihydrobenzo-1, 4-dioxinyl, imidazo(2,1-b)(1,3)thiazole, pyrimidinylphenyl, pyridinylphenyl, and benzo-1,3-dioxolyl.

9. A compound of claim 8 wherein in —$C_{0-10}$ alkylheterocyclyl, the heterocyclyl moiety is selected from pyridinyl, phenyl, thiazolyl, oxadiazolyl, benzothiazolyl, oxazolyl, quinolyl, benzothienyl, pyrazolyl, pyrazinyl, and pyridinyl.

10. A compound of claim 8 wherein —$C_{0-10}$ alkylheterocyclyl is —$C_{1-3}$alkylheterocyclyl.

11. A compound according to claim 1 selected from:
N-({1-[(6-chloropyridin-3-yl)methyl]-4-hydroxy-2-oxo-1,2,5,7-tetrahydrothieno[3,4-b]pyridin-3-yl}carbonyl)glycine;
N-{[1-(4-bromobenzyl)-4-hydroxy-2-oxo-1,2,5,7-tetrahydrothieno[3,4-b]pyridin-3-yl]carbonyl}glycine;
N-{[1-(4-cyanobenzyl)-4-hydroxy-2-oxo-1,2,5,7-tetrahydrothieno[3,4-b]pyridin-3-yl]carbonyl}glycine;
N-({4-hydroxy-2-oxo-1-[4-(trifluoromethyl)benzyl]-1,2,5,7-tetrahydrothieno[3,4-b]pyridin-3-yl}carbonyl)glycine;
N-[(4-hydroxy-2-oxo-1-{[6-(trifluoromethyl)pyridin-3-yl]methyl}-1,2,5,7-tetrahydrothieno[3,4-b]pyridin-3-yl)carbonyl]glycine;
N-({4-hydroxy-1-[4-(methylsulfonyl)benzyl]-2-oxo-1,2,5,7-tetrahydrothieno[3,4-b]pyridin-3-yl}carbonyl)glycine;
N-({4-hydroxy-2-oxo-1-[(4-phenyl-1,3-thiazol-2-yl)methyl]-1,2,5,7-tetrahydrothieno[3,4-b]pyridin-3-yl}carbonyl)glycine
N-{[4-hydroxy-1-(4-isopropylbenzyl)-2-oxo-1,2,5,7-tetrahydrothieno[3,4-b]pyridin-3-yl]carbonyl}glycine;
N-{[1-(4-tert-butylbenzyl)-4-hydroxy-2-oxo-1,2,5,7-tetrahydrothieno[3,4-b]pyridin-3-yl]carbonyl}glycine;
N-({4-hydroxy-2-oxo-1-[(5-phenyl-1,2,4-oxadiazol-3-yl)methyl]-1,2,5,7-tetrahydrothieno[3,4-b]pyridin-3-yl}carbonyl)glycine;
N-{[1-(1,3-benzothiazol-2-ylmethyl)-4-hydroxy-2-oxo-1,2,5,7-tetrahydrothieno[3,4-b]pyridin-3-yl]carbonyl}glycine;
N-{[1-(4-bromophenyl)-4-hydroxy-2-oxo-1,2,5,7-tetrahydrothieno[3,4-b]pyridin-3-yl]carbonyl}glycine;
N-({1-[3-fluoro-5-(trifluoromethyl)benzyl]-4-hydroxy-2-oxo-1,2,5,7-tetrahydrothieno[3,4-b]pyridin-3-yl}carbonyl)glycine;
N-{[1-(3-chlorobenzyl)-4-hydroxy-2-oxo-1,2,5,7-tetrahydrothieno[3,4-b]pyridin-3-yl]carbonyl}glycine;
N-{[1-(4-chloro-2-methylbenzyl)-4-hydroxy-2-oxo-1,2,5,7-tetrahydrothieno[3,4-b]pyridin-3-yl]carbonyl}glycine;
N-{[1-(4-chlorobenzyl)-4-hydroxy-2-oxo-1,2,5,7-tetrahydrothieno[3,4-b]pyridin-3-yl]carbonyl}glycine;
N-{[1-(4-ethylbenzyl)-4-hydroxy-2-oxo-1,2,5,7-tetrahydrothieno[3,4-b]pyridin-3-yl]carbonyl}glycine;
N-({1-[4-chloro-3-(trifluoromethyl)benzyl]-4-hydroxy-2-oxo-1,2,5,7-tetrahydrothieno[3,4-b]pyridin-3-yl}carbonyl)glycine;
N-{[1-(3,4-dichlorobenzyl)-4-hydroxy-2-oxo-1,2,5,7-tetrahydrothieno[3,4-b]pyridin-3-yl]carbonyl}glycine;
N-({4-hydroxy-2-oxo-1-[4-(trifluoromethoxy)benzyl]-1,2,5,7-tetrahydrothieno[3,4-b]pyridin-3-yl}carbonyl)glycine;
N-({4-hydroxy-2-oxo-1-[(2-phenyl-1,3-oxazol-4-yl)methyl]-1,2,5,7-tetrahydrothieno[3,4-b]pyridin-3-yl}carbonyl)glycine;
N-{[1-(1-benzothien-2-ylmethyl)-4-hydroxy-2-oxo-1,2,5,7-tetrahydrothieno[3,4-b]pyridin-3-yl]carbonyl}glycine;
N-({4-hydroxy-2-oxo-1-[4-(1H-pyrazol-1-yl)benzyl]-1,2,5,7-tetrahydrothieno[3,4-b]pyridin-3-yl}carbonyl)glycine;
N-({4-hydroxy-2-oxo-1-[(1-phenyl-1H-pyrazol-4-yl)methyl]-1,2,5,7-tetrahydrothieno[3,4-b]pyridin-3-yl}carbonyl)glycine;
N-({4-hydroxy-1-[(4'-methylbiphenyl-4-yl)methyl]-2-oxo-1,2,5,7-tetrahydrothieno[3,4-b]pyridin-3-yl}carbonyl)glycine;
N-[(1-{[5-(2-fluorophenyl)pyrazin-2-yl]methyl}-4-hydroxy-2-oxo-1,2,5,7-tetrahydrothieno[3,4-b]pyridin-3-yl)carbonyl]glycine;
N-({4-hydroxy-2-oxo-1-[4-(1H-pyrazol-5-yl)benzyl]-1,2,5,7-tetrahydrothieno[3,4-b]pyridin-3-yl}carbonyl)glycine;
N-({1-[(4'-acetylbiphenyl-4-yl)methyl]-4-hydroxy-2-oxo-1,2,5,7-tetrahydrothieno[3,4-b]pyridin-3-yl}carbonyl)glycine;
N-{[1-(biphenyl-4-ylmethyl)-4-hydroxy-2-oxo-1,2,5,7-tetrahydrothieno[3,4-b]pyridin-3-yl]carbonyl}glycine;
N-({1-[(4'-chlorobiphenyl-4-yl)methyl]-4-hydroxy-2-oxo-1,2,5,7-tetrahydrothieno[3,4-b]pyridin-3-yl}carbonyl)glycine;
N-({1-[4-(3,5-dimethyl-1H-pyrazol-4-yl)benzyl]-4-hydroxy-2-oxo-1,2,5,7-tetrahydrothieno[3,4-b]pyridin-3-yl}carbonyl)glycine;
N-({1-[4-(4-fluorophenoxy)benzyl]-4-hydroxy-2-oxo-1,2,5,7-tetrahydrothieno[3,4-b]pyridin-3-yl}carbonyl)glycine;
N-({1-[4-(4-chlorophenoxy)benzyl]-4-hydroxy-2-oxo-1,2,5,7-tetrahydrothieno[3,4-b]pyridin-3-yl}carbonyl)glycine;
N-({1-[(4'-ethoxybiphenyl-4-yl)methyl]-4-hydroxy-2-oxo-1,2,5,7-tetrahydrothieno[3,4-b]pyridin-3-yl}carbonyl)glycine;
N-({4-hydroxy-2-oxo-1-[4-(2-thienyl)benzyl]-1,2,5,7-tetrahydrothieno[3,4-b]pyridin-3-yl}carbonyl)glycine;
N-[(4-hydroxy-2-oxo-1-{[4'-(trifluoromethoxy)biphenyl-4-yl]methyl}-1,2,5,7-tetrahydrothieno[3,4-b]pyridin-3-yl)carbonyl]glycine;
N-{[1-({2'-[(diethylamino)carbonyl]biphenyl-4-yl}methyl)-4-hydroxy-2-oxo-1,2,5,7-tetrahydrothieno[3,4-b]pyridin-3-yl]carbonyl}glycine;
N-({4-hydroxy-2-oxo-1-[4'-(trifluoromethoxy)biphenyl-4-yl]-1,2,5,7-tetrahydrothieno[3,4-b]pyridin-3-yl}carbonyl)glycine;

N-[(1-{[6-(3-chlorophenyl)pyridinium-3-yl]methyl}-4-hydroxy-2-oxo-1,2,5,7-tetrahydrothieno[3,4-b]pyridin-3-yl)carbonyl]glycine trifluoroacetate;

N-[(1-{[6-(4-fluorophenyl)pyridinium-3-yl]methyl}-4-hydroxy-2-oxo-1,2,5,7-tetrahydrothieno[3,4-b]pyridin-3-yl)carbonyl]glycine trifluoroacetate;

N-[(1-{[6-(2-chlorophenyl)pyridinium-3-yl]methyl}-4-hydroxy-2-oxo-1,2,5,7-tetrahydrothieno[3,4-b]pyridin-3-yl)carbonyl]glycine trifluoroacetate;

N-({4-hydroxy-2-oxo-1-[3'-(trifluoromethoxy)biphenyl-4-yl]-1,2,5,7-tetrahydrothieno[3,4-b]pyridin-3-yl}carbonyl)glycine;

N-[(1-{[6-(2-fluorophenyl)pyridin-3-yl]methyl}-4-hydroxy-2-oxo-1,2,5,7-tetrahydrothieno[3,4-b]pyridin-3-yl)carbonyl]glycine;

N-{[4-hydroxy-2-oxo-1-({6-[4-(trifluoromethyl)phenyl]pyridinium-3-yl}methyl)-1,2,5,7-tetrahydrothieno[3,4-b]pyridin-3-yl]carbonyl}glycine trifluoroacetate;

N-{[4-hydroxy-2-oxo-1-({6-[2-(trifluoromethyl)phenyl]pyridinium-3-yl}methyl)-1,2,5,7-tetrahydrothieno[3,4-b]pyridin-3-yl]carbonyl}glycine trifluoroacetate;

N-({1-[(3'-cyanobiphenyl-4-yl)methyl]-4-hydroxy-2-oxo-1,2,5,7-tetrahydrothieno[3,4-b]pyridin-3-yl}carbonyl)glycine;

N-{[4-hydroxy-1-({6-[2-(methylthio)phenyl]pyridinium-3-yl}methyl)-2-oxo-1,2,5,7-tetrahydrothieno[3,4-b]pyridin-3-yl]carbonyl}glycine trifluoroacetate;

N-[(4-hydroxy-1-{[6-(2-methylphenyl)pyridinium-3-yl]methyl}-2-oxo-1,2,5,7-tetrahydrothieno[3,4-b]pyridin-3-yl)carbonyl]glycine trifluoroacetate;

N-{[4-hydroxy-2-oxo-1-({6-[3-(trifluoromethoxy)phenyl]pyridinium-3-yl}methyl)-1,2,5,7-tetrahydrothieno[3,4-b]pyridin-3-yl]carbonyl}glycine trifluoroacetate;

N-[(1-{[6-(2-ethylphenyl)pyridinium-3-yl]methyl}-4-hydroxy-2-oxo-1,2,5,7-tetrahydrothieno[3,4-b]pyridin-3-yl)carbonyl]glycine trifluoroacetate;

N-[(1-{[6-(2,5-difluorophenyl)pyridinium-3-yl]methyl}-4-hydroxy-2-oxo-1,2,5,7-tetrahydrothieno[3,4-b]pyridin-3-yl)carbonyl]glycine trifluoroacetate;

N-{[4-hydroxy-2-oxo-1-(4-quinolinium-5-ylbenzyl)-1,2,5,7-tetrahydrothieno[3,4-b]pyridin-3-yl]carbonyl}glycine chloride;

N-[(1-{[5-(2-chlorophenyl)pyrazin-2-yl]methyl}-4-hydroxy-2-oxo-1,2,5,7-tetrahydrothieno[3,4-b]pyridin-3-yl)carbonyl]glycine;

N-[(4-hydroxy-1-{[5-(2-methylphenyl)pyrazin-2-yl]methyl}-2-oxo-1,2,5,7-tetrahydrothieno[3,4-b]pyridin-3-yl)carbonyl]glycine;

N-{[4-hydroxy-1-({5-[2-(methylthio)phenyl]pyrazin-2-yl}methyl)-2-oxo-1,2,5,7-tetrahydrothieno[3,4-b]pyridin-3-yl]carbonyl}glycine;

N-[(1-{[5-(2,5-difluorophenyl)pyrazin-2-yl]methyl}-4-hydroxy-2-oxo-1,2,5,7-tetrahydrothieno[3,4-b]pyridin-3-yl)carbonyl]glycine;

N-{[4-hydroxy-2-oxo-1-({5-[2-(trifluoromethyl)phenyl]pyrazin-2-yl}methyl)-1,2,5,7-tetrahydrothieno[3,4-b]pyridin-3-yl]carbonyl}glycine;

N-({4-hydroxy-1-[(4'-methylbiphenyl-4-yl)methyl]-6,6-dioxido-2-oxo-1,2,5,7-tetrahydrothieno[3,4-b]pyridin-3-yl}carbonyl)glycine;

N-({4-hydroxy-1-[(4'-methylbiphenyl-4-yl)methyl]-6-oxido-2-oxo-1,2,5,7-tetrahydrothieno[3,4-b]pyridin-3-yl}carbonyl)glycine;

N-{[1-(4-chlorobenzyl)-4-hydroxy-6,6-dioxido-2-oxo-1,2,5,7-tetrahydrothieno[3,4-b]pyridin-3-yl]carbonyl}glycine;

N-{[4-hydroxy-1-(4-isopropylbenzyl)-6,6-dioxido-2-oxo-1,2,5,7-tetrahydrothieno[3,4-b]pyridin-3-yl]carbonyl}glycine;

N-({4-hydroxy-6,6-dioxido-2-oxo-1-[(4-phenyl-1,3-thiazol-2-yl)methyl]-1,2,5,7-tetrahydrothieno[3,4-b]pyridin-3-yl}carbonyl)glycine;

N-({4-hydroxy-6,6-dioxido-2-oxo-1-[4-(trifluoromethyl)benzyl]-1,2,5,7-tetrahydrothieno[3,4-b]pyridin-3-yl}carbonyl)glycine;

N-{[1-(biphenyl-4-ylmethyl)-4-hydroxy-6,6-dioxido-2-oxo-1,2,5,7-tetrahydrothieno[3,4-b]pyridin-3-yl]carbonyl}glycine;

N-({4-hydroxy-6,6-dioxido-2-oxo-1-[4-(trifluoromethoxy)benzyl]-1,2,5,7-tetrahydrothieno[3,4-b]pyridin-3-yl}carbonyl)glycine;

N-{[1-(4-ethylbenzyl)-4-hydroxy-6,6-dioxido-2-oxo-1,2,5,7-tetrahydrothieno[3,4-b]pyridin-3-yl]carbonyl}glycine; and pharmaceutically acceptable salts thereof.

12. A pharmaceutical composition comprising a compound of claim 1 and pharmaceutically acceptable carrier.

13. A method of enhancing endogenous production of erythropoietin in a mammal which comprises administering to the mammal an amount of a compound of claim 1, or a pharmaceutically acceptable salt thereof, that is effective for enhancing endogenous production of erythropoietin.

14. A method for the treatment of anemia in a mammal which comprises administering to the mammal an effective amount of a compound of claim 1, or a pharmaceutically acceptable salt thereof.

* * * * *